(12) United States Patent
Breitler et al.

(10) Patent No.: US 11,021,503 B2
(45) Date of Patent: Jun. 1, 2021

(54) PROCESS FOR GALNAC OLIGONUCLEOTIDE CONJUGATES

(71) Applicant: Hoffmann-La Roche Inc., Little Falls, NJ (US)

(72) Inventors: Simon Breitler, Basel (CH); Joerg Lill, Basel (CH); Kurt Puentener, Basel (CH); René Trussardi, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/690,615

(22) Filed: Nov. 21, 2019

(65) Prior Publication Data
US 2020/0079807 A1 Mar. 12, 2020

Related U.S. Application Data

(63) Continuation of application No. PCT/EP2018/063264, filed on May 22, 2018.

(30) Foreign Application Priority Data

May 23, 2017 (WO) .................. PCT/EP2017/062318

(51) Int. Cl.
| | |
|---|---|
| *C07H 1/00* | (2006.01) |
| *A61K 47/54* | (2017.01) |
| *C07H 21/02* | (2006.01) |
| *C07H 21/04* | (2006.01) |

(52) U.S. Cl.
CPC ............. *C07H 1/00* (2013.01); *A61K 47/549* (2017.08); *C07H 21/02* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 8,541,569 | B2 | 9/2013 | Srivastava et al. |
| 2004/0033973 | A1 | 2/2004 | Manoharan et al. |
| 2011/0207799 | A1 | 8/2011 | Rozema et al. |
| 2015/0299696 | A1* | 10/2015 | Carr ..................... C12N 15/111 514/44 A |
| 2018/0162894 | A1 | 6/2018 | Lill et al. |

FOREIGN PATENT DOCUMENTS

| | | |
|---|---|---|
| WO | 92/06103 | 4/1992 |
| WO | 2006/029023 A2 | 3/2006 |
| WO | 2010/108125 A2 | 9/2010 |
| WO | 2011/104169 A1 | 9/2011 |
| WO | 2012/083046 A2 | 6/2012 |
| WO | 2012/083185 A2 | 6/2012 |
| WO | 2014/076195 A1 | 5/2014 |
| WO | 2014/118267 A1 | 8/2014 |
| WO | 2014/179620 A1 | 11/2014 |
| WO | 2014/207232 A1 | 12/2014 |
| WO | 2015/071388 A1 | 5/2015 |
| WO | 2015/168589 A2 | 11/2015 |
| WO | 2015/173208 A2 | 11/2015 |
| WO | 2017/021385 A1 | 2/2017 |
| WO | 2017/055423 A1 | 6/2017 |
| WO | 2019/145543 A1 | 8/2019 |
| WO | 2019/175126 A1 | 9/2019 |

OTHER PUBLICATIONS

Wincott, Nucleic Acids Research, 1995, vol. 23, No. 14, pp. 2677-2684. (Year: 1995).*
Ye, Biopolymers. 2005;80(2-3):172-8. (Year: 2005).*
The Glen Report, Glen Research, vol. 23, No. 1, May 2011. (Year: 2011).*
Bannwarth et al., "Formation of Carboxamides with N,N,N',N'-Tetramethyl (Succinimido) Uronium Tetrafluoroborate in Aqueous / Organic Solvent Systems" Tetrahedron Letters 32(9):1157-1160 ( 1991).
CAS Registry entry for Registry No. 1185198-47-3, Sep. 16, 2009.
CAS Registry entry for Registry No. 133170-57-7, Apr. 12, 1991.
CAS Registry entry for Registry No. 156917-23-6, Aug. 10, 1994.
Chakravarty et al., "Plasmin-Activated Prodrugs for Cancer Chemotherapy. 2. Synthesis and Biological Activity of Peptidyl Derivatives of Doxorubicin" Journal of Medicinal Chemistry 26(5):638-644 (Jan. 1, 1983).
Han et al., "Recent development of peptide coupling reagents in organic synthesis" Tetrahedron 60(11):2447-2467 ( 2004).
International Search Report for PCT/EP2017/062318 dated Aug. 9, 2017.
International Search Report for PCT/EP2018/063264 dated Aug. 21, 2018.
International Search Report for PCT/EP2019/052014 dated Apr. 17, 2019.
International Search Report for PCT/EP2019/056068 dated May 13, 2019.
International Search Report for PCT/EP2016/068361 (dated Sep. 19, 2016).
Iselin et al., "Derivate von L-Methionin-sulfoxyd and ihre Verwendung für Peptidsynthesen" Helvetica Chimica ACTA 44(1):61-78 (Oct. 24, 1961).
Kessler and Iselin, "Selektive Spaltung substituierter Phenylsulfenyl-Schutzgruppen bei Peptidsynthesen" Helvetica Chimica ACTA 49(4):1330-1344 (Jan. 1, 1966).
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron 54(14):3607-3630 (1998).

(Continued)

*Primary Examiner* — Layla D Berry
(74) *Attorney, Agent, or Firm* — Kevin M. Clark

(57) ABSTRACT

The invention comprises a process for the preparation of therapeutically valuable GalNAc cluster oligonucleotide conjugates. The process comprises the coupling of an alkali metal salt, earth alkali metal salt or a tetraalkylammonium salt of an oligonucleotide with a GalNAc cluster compound or with a salt thereof and a subsequent purification.

17 Claims, No Drawings

Specification includes a Sequence Listing.

(56) References Cited

OTHER PUBLICATIONS

MacMillian et al., "Evaluation of alternative solvents in common amide coupling reactions: replacement of dichloromethane and N,N-dimethylformamide" Green Chemistry 15:596-600 ( 2013).
Maruzen et al., "Synthesis of Organic Compounds IV-Carboxylic Acid" The Chemical Society of Japan 5th Edition:121-123 ( 2005).
Nitecki et al., "The Synthesis of the Pentapeptide Related to the gm(a) Antigen of human gamma G-Globulin" Australian Journal of Chemistry 22(4):871-874 (Jan. 1, 1969).
Prakash et al., "Comprehensive Structure—Activity Relationship of Triantennary N-Acetylgalactosamine Conjugated Antisense Oligonucleotides for Targeted Delivery to Hepatocytes" Journal of Medicinal Chemistry 59:2718-2733 ( 2016).
Prakash et al., "Solid-phase synthesis of 50-triantennary N-acetylgalactosamine conjugated antisense oligonucleotides using phosphoramidite chemistry" Bioorganic & Medicinal Chemistry Letters 25(19):4127-4130 (Aug. 8, 2015).
Schiesser et al., "Synthesis and DNA-Damaging Properties of Cisplatin-N-Mustard Conjugates" European Journal of Organic Chemistry 2015(12):2654-2660 (Apr. 13, 2015).
Zhao et al., "N-(2-Chloro-9H-purin-6-yl)-N-cyclopropylglycylamino acids and derivatives Synthesis,evaluation as a class of novel analgesics, and 3D QSAR analysis" Bioorganic & Medicinal Chemistry 17:6305-6310 (Sep. 1, 2009).

* cited by examiner

PROCESS FOR GALNAC OLIGONUCLEOTIDE CONJUGATES

CROSS-REFERENCE TO RELATED APPLICATIONS

This application is a continuation of International Application No. PCT/EP2018/063264, filed May 22, 2018, the entire contents of which are incorporated herein by reference, which claims benefit under 35 U.S.C. § 119 to International Application No. PCT/EP2017/062318 filed May 23, 2017.

SEQUENCE LISTING

This application contains a Sequence Listing which has been submitted electronically in ASCII format and is hereby incorporated by reference in its entirety. Said ASCII copy, created on Nov. 11, 2019, is named "P33656_US_Sequence_Listing.txt" and is 4,096 bytes in size.

The invention relates to a new process for the preparation of a GalNAc cluster oligonucleotide conjugate.

Recently there has been considerable focus in the conjugation of oligonucleotides with non-nucleotide moieties which add additional functionality to the oligonucleotide, for example, enabling targeting of therapeutic oligonucleotides to specific organs and tissues in vivo. For targeting to liver hepatocytes trivalent GalNAc conjugation moieties capable of binding to asialoglycoprotein receptors have been found to allow for vastly reduced dosages whilst delivering effective therapeutic action. Such GalNAc cluster antisense conjugates are e.g. described in the PCT Publication WO 2012/083046 or in the US Patent Application Publication US 2011/0207799.

While these publications disclose processes for the preparation of GalNAc cluster oligonucleotide conjugate it was found that these processes do not meet the standard for a technical scale synthesis.

Object of the invention therefore is to provide an improved method for the preparation of GalNAc cluster oligonucleotide conjugates which meets the requirements of an industrial scale process.

The process for the preparation of a GalNAc cluster oligonucleotide conjugate comprises the steps of a) producing an oligonucleotide or an aliphatic amine salt thereof bound to a solid phase support;

b) cleaving the oligonucleotide from the support and removing the protecting groups in the presence of ammonia, thereby providing the ammonium salt of the unprotected oligonucleotide;

c) performing a salt exchange change from the ammonium salt of the oligonucleotide to an alkali metal salt, earth alkali metal salt or to a tetraalkylammonium salt of the oligonucleotide, thereby removing any free ammonia or residual aliphatic amine;

d) coupling the alkali metal salt, earth alkali metal salt or the tetraalkylammonium salt of the oligonucleotide with the GalNAc cluster compound or with a salt thereof and finally e) purifying the GalNAc-cluster oligonucleotide conjugate.

The following definitions are set forth to illustrate and define the meaning and scope of the various terms used to describe the invention herein.

Whenever a chiral carbon is present in a chemical structure, it is intended that all stereoisomers associated with that chiral carbon are encompassed by the structure as pure stereoisomers as well as mixtures thereof.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "$C_{1-12}$-alkyl" denotes a monovalent linear or branched saturated hydrocarbon group of 1 to 12 carbon atoms, and in more particular embodiments 1 to 7 carbon atoms. Examples of alkyl include methyl, ethyl, propyl, isopropyl, n-butyl, iso-butyl, sec-butyl, or tert-butyl and pentyl, hexyl, heptyl, octyl, nonyl, decyl, undecyl and dodecyl and its isomers.

The term "aliphatic amine" denotes a mono-, di- or tri-$C_{1-4}$-alkylamine, wherein the $C_{1-4}$-alkyl is defined as above or a cyclic aliphatic amine. Particular examples of mono-, di- or tri-$C_{1-4}$-alkylamine are ethylamine, diethylamine or triethylamine. Particular examples of cyclic aliphatic amines are the five membered cyclic aliphatic amines such as pyrrolidine or the six membered cyclic aliphatic amines such as piperidine or morpholine.

The term "amino-protecting group" denotes groups intended to protect an amino group and includes benzoyl, benzyloxycarbonyl, carbobenzyloxy (CBZ or Z), 9-fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981.

The term "hydroxy-protecting group" and the term "ester protecting group" denote groups which intended to protect a hydroxy group and include ester- and ether-forming groups, in particular tetrahydropyranyl, acyl groups, carbamoyl, benzyl and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. Preferred are the acyl groups, particularly a $C_{1-12}$-alkylcarbonyl group, more particularly a $C_{1-6}$-alkylcarbonyl group which is optionally substituted by $C_{1-6}$-alkyl or phenyl. More preferred hydroxy protecting groups can be selected from acetyl, pivaloyl or benzoyl, whereby acetyl is the most preferred hydroxy protecting group.

The term "alkali" encompasses the alkali metals lithium, sodium and potassium, particularly sodium and potassium with preference to sodium.

The term "earth alkali" encompasses the earth alkali metals calcium and magnesium, but particularly calcium.

The term 5'amino modified is used in connection with the term 5' amino-modified oligonucleotide and determines a reactive amino group covalently bound to a linker which, as amino linker, is attached at the 5' terminal group of an oligonucleotide. The linker preferably is an aliphatic alkyl group of 2 to 12 carbon atoms or an ethylene glycol linker containing 1 to 10 ethylene glycol units.

The preferred 5'amino-modifier accordingly is selected from an optionally amino group protected amino $C_{2-12}$-alkyl linker or an amino ethylene glycol linker containing 1 to 10 ethylene glycol units.

Suitable amino protecting groups for the 5'amino modified oligonucleotide are trifluoroacetyl (TFA) or monomethoxytrityl (MMT).

As a rule the amino linker is introduced via a commercially available amino linker phosphoroamidite such as for instance via the TFA- or MMT-$C_6$-linker phosphoroamidites e.g. from Sigma Aldrich or via the 5' amino modifier TEG (triethyleneglycol) CE phosphoroamidite from Glen Research.

The term oligonucleotide as used herein is defined as it is generally understood by the skilled person as a molecule comprising two or more covalently linked nucleotides. For use as a therapeutically valuable oligonucleotide, oligonucleotides are typically synthesized as 7-30 nucleotides in length.

The oligonucleotides may consist of optionally modified DNA, RNA or LNA nucleoside monomers or combinations thereof.

The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, RNA or LNA nucleoside by the introduction of one or more modifications of the sugar moiety or the nucleo base moiety. In a preferred embodiment the modified nucleoside comprise a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleosides are as a rule linked by a phosphodiester (P=O) and/or a phosphorothioate (P=S) internucleoside linkage which covalently couples two nucleosides together.

Accordingly in some oligonucleotides all internucleoside linkages may consist of a phosphodiester (P=O), in other oligonucleotides all internucleoside linkages may consist of a phosphorothioate (P=S) or in still other oligonucleotides the sequence of internucleoside linkages vary and comprise both phosphodiester (P=O) and phosphorothioate (P=S) internucleoside.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}C$ (5-methyl cytosine) for LNA nucleoside and with small letters a,t,g,c and $^{Me}c$ for DNA nucleosides. Modified nucleobases include but are not limited to nucleobases carrying protecting groups such as tert.butylphenoxyacetyl, phenoxyacetyl, benzoyl, acetyl, isobutyryl or dimethylformamidino (see Wikipedia, Phosphoramidit-Synthese, https://de.wikipedia.org/wiki/Phosphoramidit-Synthese of Mar. 24, 2016).

Preferably the oligonucleotide consists of optionally modified DNA or LNA nucleoside monomers or combinations thereof and is 10 to 25 nucleotides in length.

Step a):

Step a) requires the production of an oligonucleotide or an aliphatic amine salt thereof on a solid phase support.

The principles of the oligonucleotide synthesis are well known in the art and well described in literature and public for a like Wikipedia (see e.g. Oligonucleotide synthesis; Wikipedia, the free encyclopedia; https://en.wikipedia.org/wiki/Oligonucleotide_synthesis, of Mar. 15, 2016).

Larger scale oligonucleotide synthesis nowadays is carried automatically using computer controlled synthesizers.

As a rule oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase®HL support from Kinovate.

The oligonucleotide synthesis in principle is a stepwise addition of nucleotide residues to the 5'-terminus of the growing chain until the desired sequence is assembled.

As a rule each addition is referred to as a synthetic cycle and in principle consists of the chemical reactions $a_1$) de-blocking the protected hydroxyl group on the solid support, $a_2$) coupling the first nucleoside as activated phosphoramidite with the free hydroxyl group on the solid support, $a_3$) oxidizing or sulfurizing the respective P-linked nucleoside to form the respective phosphotriester (P=O) or the respective phosphorothioate (P=S);

$a_4$) optionally, capping any unreacted hydroxyl groups on the solid support;

$a_5$) de-blocking the 5' hydroxyl group of the first nucleoside attached to the solid support;

$a_6$) coupling the second nucleoside as activated phosphoramidite to form the respective P-linked dimer;

$a_7$) oxidizing or sulfurizing the respective P-linked dinucleoside to form the respective phosphotriester (P=O) or the respective phosphorothioate (P=S);

$a_8$) optionally, capping any unreacted 5' hydroxyl groups;

$a_9$) repeating the previous steps as to as until the desired sequence is assembled.

The phosphoroamidite monomers applied are shown below and represent a preferred embodiment of the present invention.
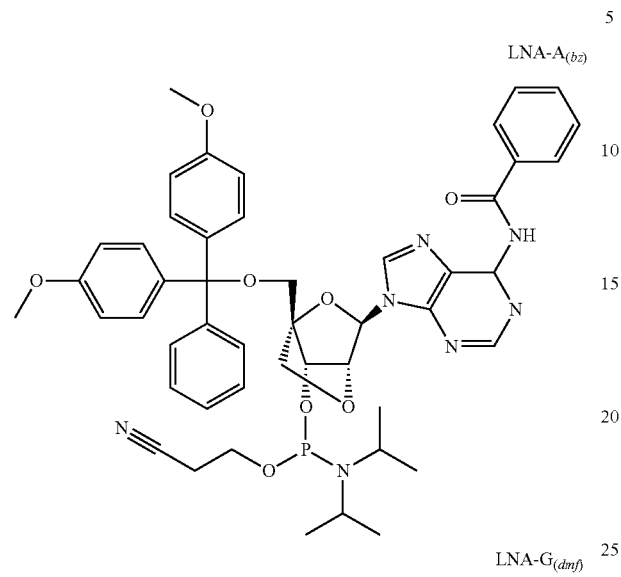
LNA-A(bz)
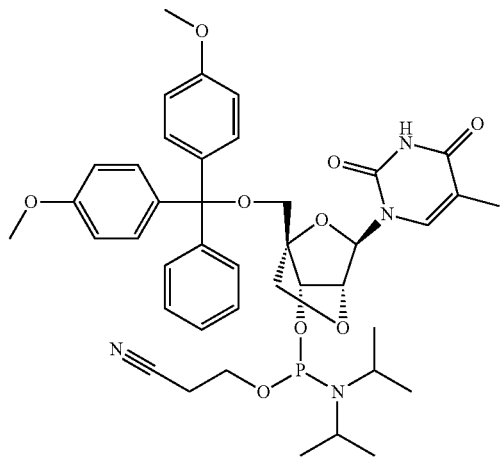
LNA-T
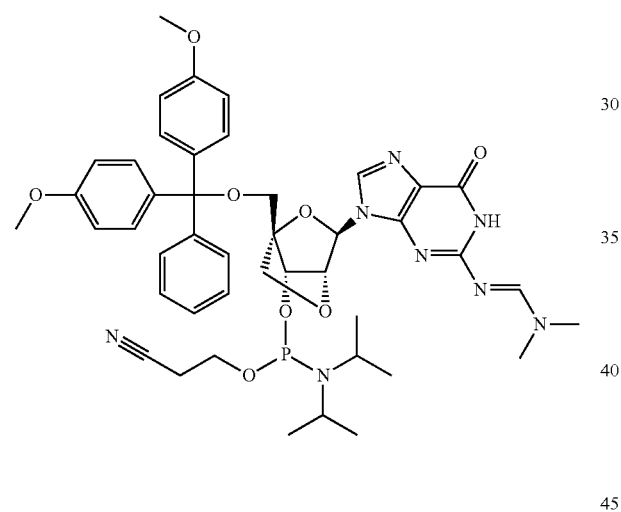
LNA-G(dmf)
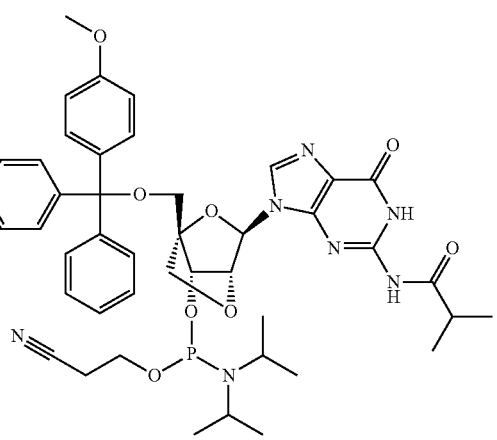
LNA-G(ibu)
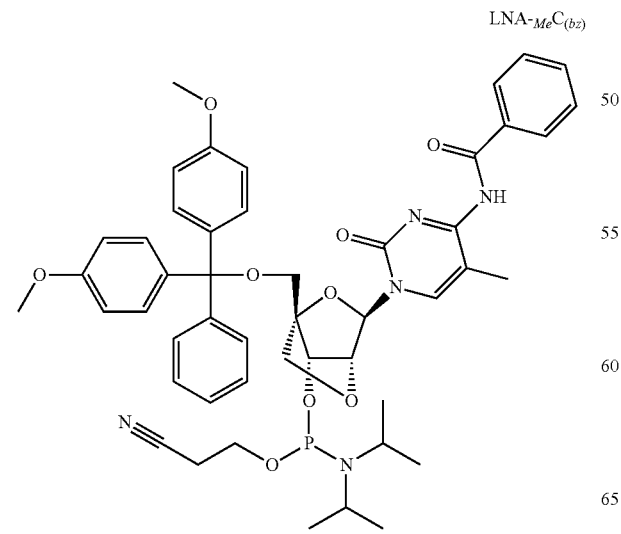
LNA-MeC(bz)
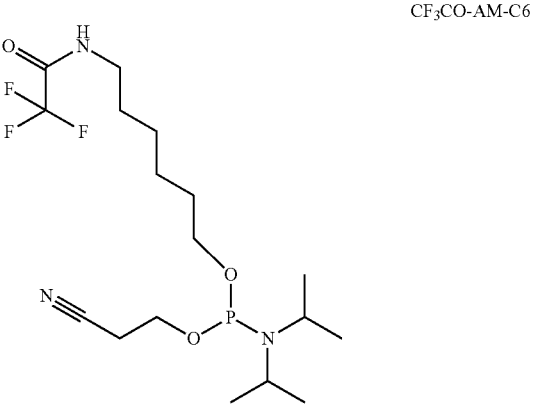
CF₃CO-AM-C6

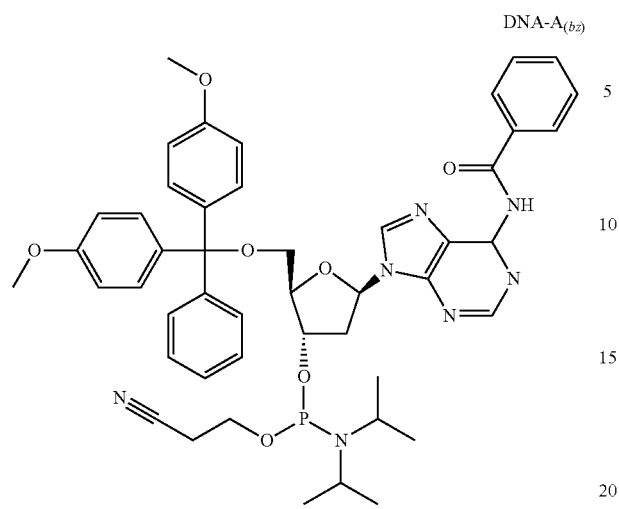

DNA-A(bz)

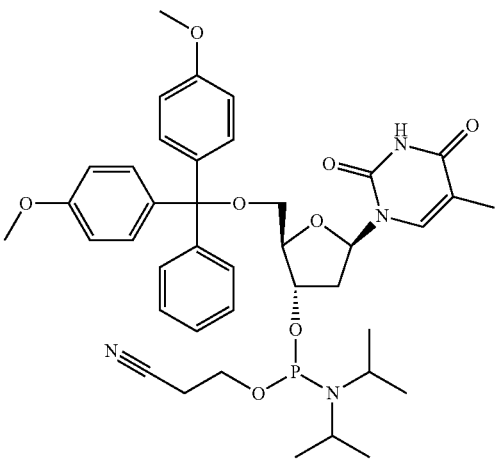

DNA-T

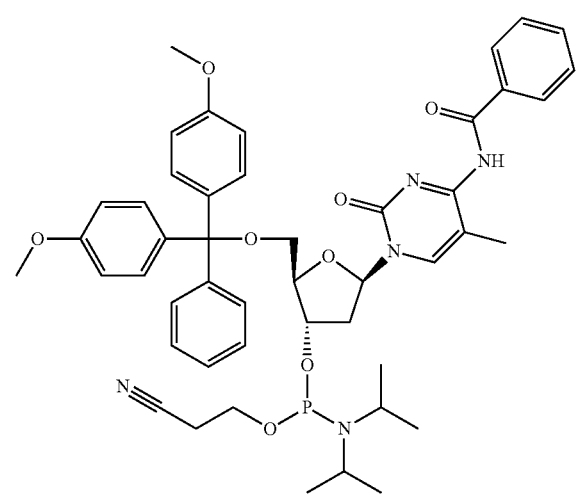

DNA-G(ibu)

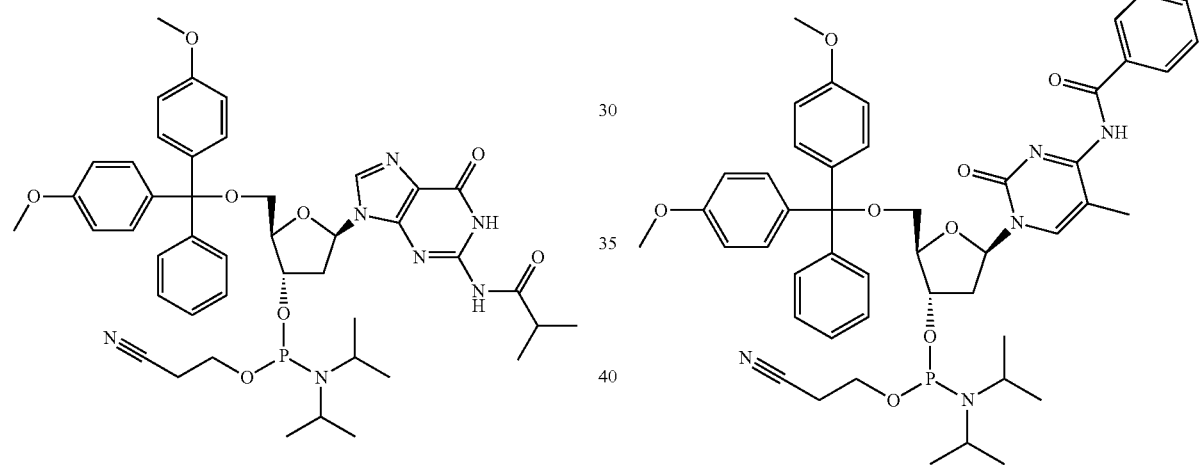

DNA-MeC(bz)

DNA-C(bz)

In a preferred embodiment of the present invention the oligonucleotide is produced in the form of an aliphatic amine salt.

The aliphatic amine salt is obtained following the deprotection step (removal of the 2-cyano ethyl P-protecting group) with the respective aliphatic amine.

Suitable aliphatic amines are the mono-, di- or tri-$C_{1-4}$-alkylamines or cyclic aliphatic amines as defined before.

Preferably the mono-, di- or tri-$C_{1-4}$-alkylamines, more preferably the di-$C_{1-4}$-alkylamines and particularly diethylamine is used.

Accordingly, in a more preferred embodiment of the present invention the oligonucleotide is produced in the form of the diethyl amine salt.

Step b):

Step b) requires cleaving the oligonucleotide from the support and removing the protecting groups.

The cleaving of the oligonucleotide from the support and the removing of the protecting groups (nucleobase protecting groups and amino modifier protecting group) is expediently effected with aqueous ammonia, thereby providing the ammonium salt of the oligonucleotide. As a rule a concentrated aqueous ammonia solution and elevated reaction temperatures between 40° C. and 80° C. are applied.

The crude ammonium salt of the oligonucleotide can then be obtained via separation from the reaction mixture by filtration, a washing step with water and/or an aliphatic alcohol and subsequent removal of the solvent by evaporation.

Step c):

Step c) requires performing a salt exchange change from the ammonium salt of the oligonucleotide to an alkali metal salt, earth alkali metal salt or to a tetraalkylammonium salt of the oligonucleotide, thereby removing any free ammonia or residual aliphatic amine.

According to one embodiment of the present invention the alkali metal salt is formed. The salt exchange is then expediently performed with an alkali metal hydroxide.

Suitable alkali hydroxides are lithium hydroxide, sodium hydroxide or potassium hydroxide, but preferably sodium hydroxide.

As a rule the salt exchange happens at room temperature or at a slightly elevated temperature in an aqueous environment, therefore an aqueous solutions of the respective hydroxide is preferably applied.

According to another embodiment of the present invention the earth alkali metal salt is formed. The salt exchange is then expediently performed with an aqueous earth alkali metal hydroxide.

Suitable earth alkali metal hydroxides are calcium hydroxide or magnesium hydroxide, but preferably calcium hydroxide.

As a rule the salt exchange happens at room temperature or at a slightly elevated temperature in an aqueous environment, therefore an aqueous solutions of the respective hydroxide is preferably applied.

In a preferred embodiment the alkali metal salt, more preferably the sodium salt of the oligonucleotide is formed.

The work up of the resulting aqueous solution of the alkalimetal salt or the earth alkali metal salt of the oligonucleotide is very important in that any free ammonia or residual aliphatic amine is effectively removed.

Therefore, according to one method the aqueous solution of the alkalimetal salt or of the earth alkali metal salt can be isolated by evaporating the water. Aceotropic removal of remaining water with the help of a suitable organic solvent such as 2-methyl-2-butanol and subsequent evaporation can provide a crude alkali metal salt of the oligonucleotide. Further digestion with an aliphatic alcohol like methanol or ethanol, filtration and washing with the respective aliphatic alcohol allows obtaining an alkali metal salt or an earth alkali metal salt of the oligonucleotide which is substantially free of ammonia and residual aliphatic amine and which therefore can readily be applied for the coupling step.

According to another method the aqueous solution of the alkalimetal salt or of the earth alkali metal salt can be isolated by a continuous partial evaporation (by constant volume and addition of water) until the pH of the vapor phase reached pH 7, thereby indicating that any remaining ammonia and or aliphatic amine has been removed. The resulting solution delivers the alkali metal salt or the earth alkali metal salt of the oligonucleotide substantially free of ammonia and residual aliphatic amine and which therefore can readily be applied for the coupling step in solution.

According to another method the aqueous solution of the alkalimetal salt or of the earth alkali metal salt can be isolated by tangential flow filtration or cross flow filtration against aqueous alkalimetal salt or earth alkali metal salt solutions, such as e.g. sodium hydroxide, sodium chloride, sodium phosphate (pH 6-8) and mixtures thereof. The resulting solution delivers the alkali metal salt or the earth alkali metal salt of the oligonucleotide substantially free of ammonia and residual aliphatic amine and which therefore can readily be applied for the coupling step in solution. Alternatively, further digestion with an aliphatic alcohol like methanol or ethanol, filtration and washing with the respective aliphatic alcohol allows obtaining an alkali metal salt or an earth alkali metal salt of the oligonucleotide which is substantially free of ammonia and residual aliphatic amine and which therefore can readily be applied for the coupling step.

The "continuous partial evaporation" method and the "tangential flow filtration or cross flow filtration" method as described above are preferred.

According to still another method the crude ammonium salt of the oligonucleotide can be purified by anion-exchange chromatography followed by desalting and concentration via tangential flow filtration or cross flow filtration. The resulting solution delivers the alkali metal salt or the earth alkali metal salt of the oligonucleotide substantially free of ammonia and residual aliphatic amine and which therefore can readily be applied for the coupling step in solution. Alternatively, lyophilization of this solution allows obtaining an alkali metal salt or an earth alkali metal salt of the oligonucleotide which is substantially free of ammonia and residual aliphatic amine and which therefore can readily be applied for the coupling step.

The purification techniques "tangential flow filtration or cross flow filtration" and "anion-exchange chromatography" are described in detail in step e) below.

According to a further embodiment of the present invention a tetraalkylammonmium salt is formed. The salt exchange is in this case expediently performed with a tetraalkylammonium hydroxide or halide, preferably with a tetra $C_{1-12}$-alkylammonium hydroxide or halide such as with tetrabutyl ammonium hydroxide or tetrabutyl ammonium bromide in a suitable organic solvent selected from methanol, dimethylsulfoxide, N,N'-dimethylformamide, dimethylacetamide, N-methyl-2-pyrrolidine, N-ethylpyrrolidone, 1,3-dimethyl-2-imidazolidinone or mixtures thereof. Preferably methanol or dimethyl sulfoxide or mixtures thereof are used. In case of a mixture methanol and dimethyl sulfoxide the methanol can be removed by evaporation to obtain a tetraalkylammonium salt in an aprotic solution. This embodiment is suitable if the subsequent coupling is performed under anhydrous conditions.

Step d):

Step d) requires the coupling of the alkali metal salt, earth alkali metal salt or the tetraalkylammonium salt of the oligonucleotide with the GalNAc cluster compound or with a salt thereof.

The GalNAc cluster compound has the formula

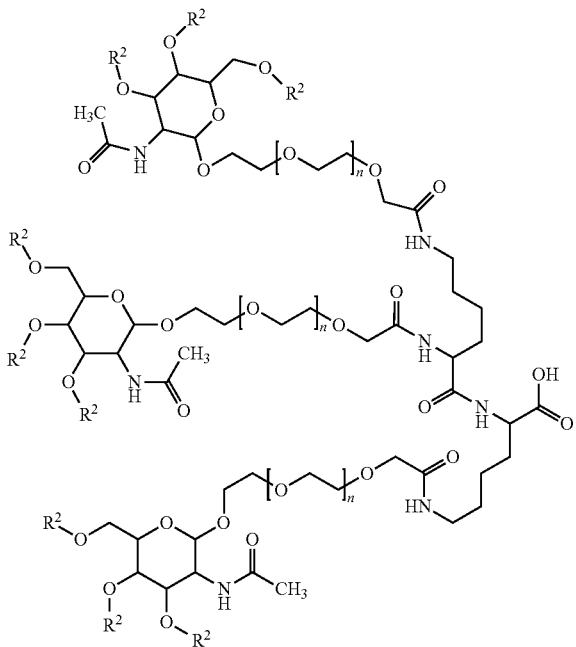

I wherein $R^2$ is hydrogen or a hydroxy protecting group and n is an integer from 0 to 10, corresponding salts, enantiomers and/or a stereoisomers thereof.

Suitable hydroxy protecting groups are acyl, particularly the $C_{1-12}$-alkylcarbonyl group, more particularly the $C_{1-6}$-alkylcarbonyl group which is optionally substituted by $C_{1-6}$-alkyl or phenyl. More preferred is acetyl, pivaloyl or benzoyl, whereby acetyl is the most preferred hydroxy protecting group.

n is preferably an integer from 0 to 5, more preferably from 1 to 3, but most preferred is 2.

In a preferred embodiment the GalNAc cluster compound of formula I is an alkali metal or earth alkali metal salt of the formula Ia,

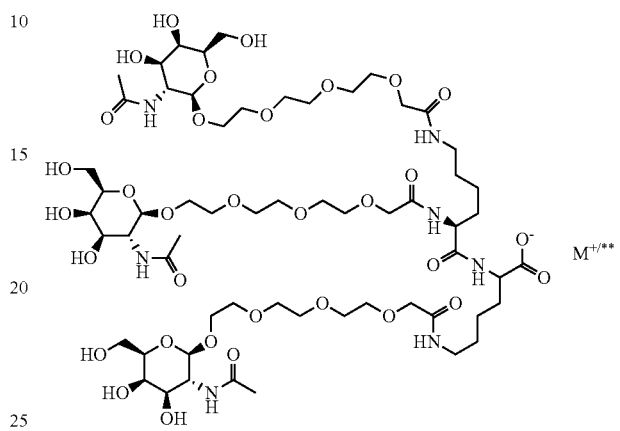

Ia wherein $M^{+/++}$ is the cation of an alkali metal or of an earth alkali metal, but preferably is sodium.

The GalNAc cluster compounds can be prepared as follows:

Initially a benzylester precursor of the GalNAc cluster compound can be prepared according to the Scheme 1 below. Subsequent hydrogenolysis of the benzylester by way of a catalytic hydrogenation with hydrogen in the presence of a hydrogenation catalyst such as for instance with palladium on charcoal delivers an acetyl-protected GalNAc cluster acid derivative of formula I.

Scheme 1:
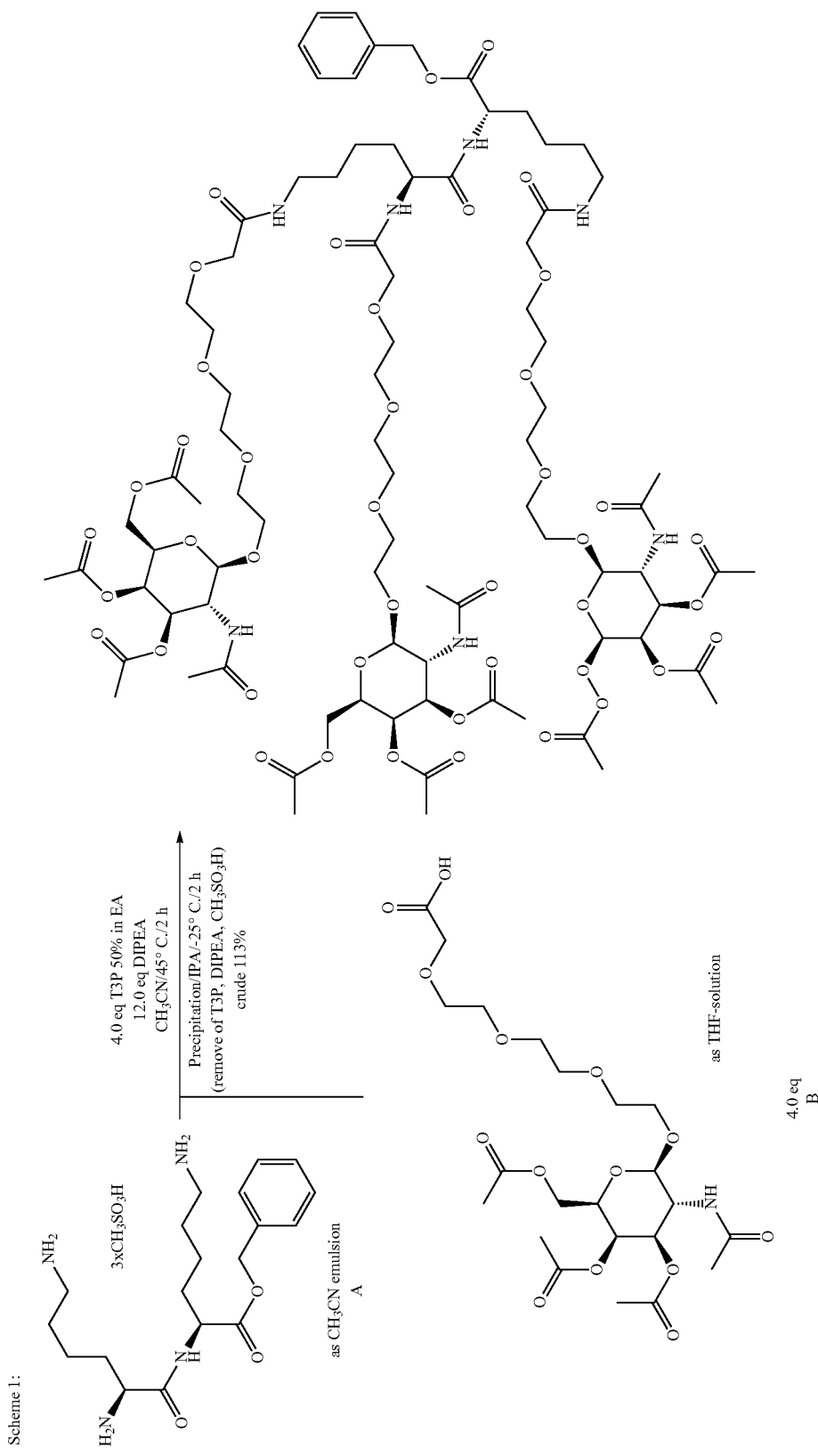

A GalNAc cluster salt of the formula I can be prepared according to scheme 2 below.
The coupling reaction of the alkali metal salt, earth alkali metal salt or the tetraalkylammonium salt of the oligonucle-
Scheme 2:
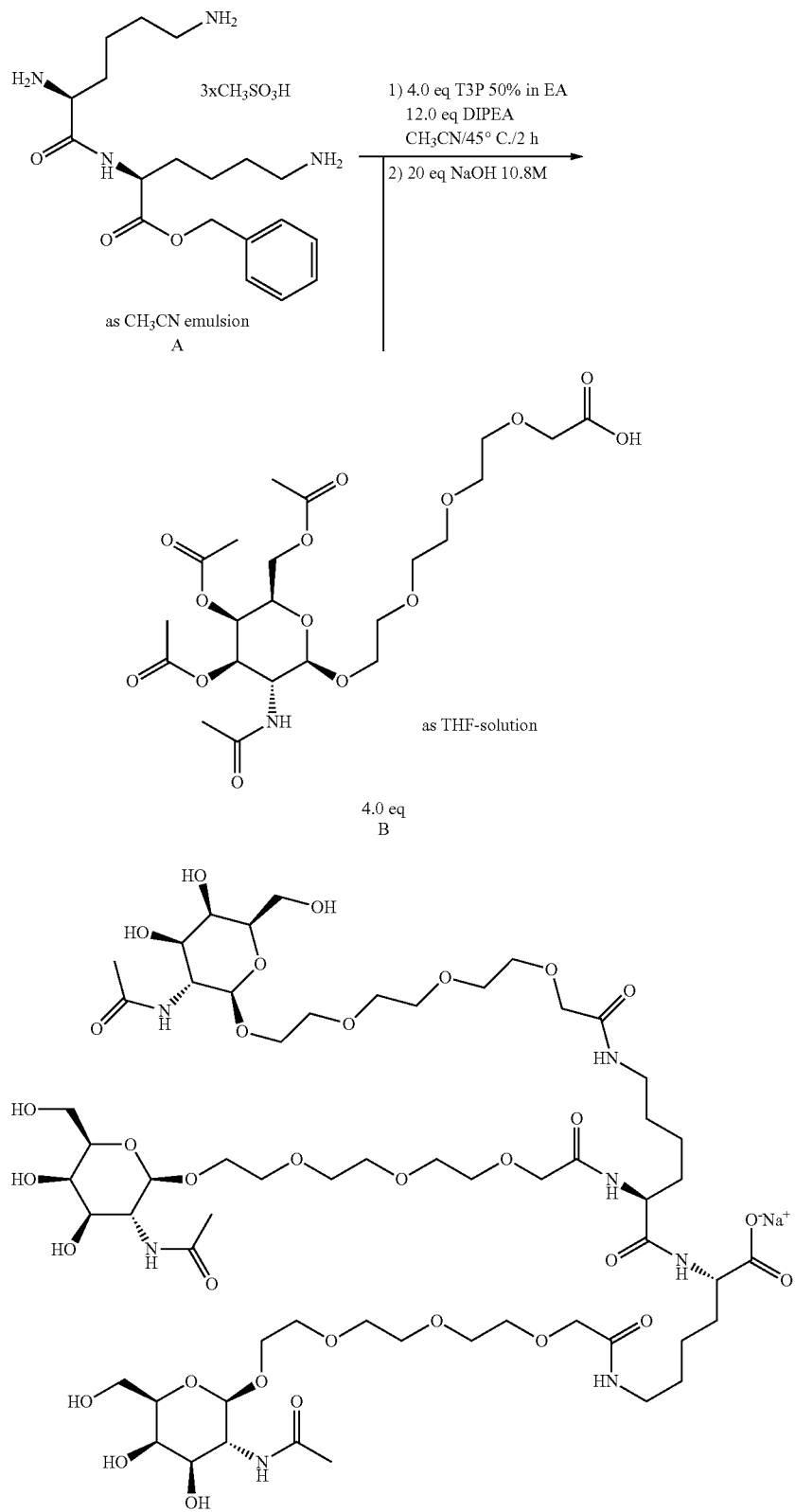

otide with the GalNAc cluster compound of formula I encompasses in a first step the activation of the GalNAc cluster compound with the coupling agent and in a second step the coupling of the activated GalNAc cluster compound with the alkali metal salt, earth alkali metal salt or the tetraalkylammonium salt of the oligonucleotide in the presence of an amine base and an organic solvent.

The coupling agent is selected from DCC (N,N'-dicyclohexylcarbodiimide) or EDC (N-(3-dimethylaminopropyl)-N'-ethylcarbodiimide-hydrochloride) or TBTU (N,N,N',N'-tetramethyl-O-(benzotriazol-1-yl)uronium tetrafluoroborate, HBTU (2-(1H-benzotriazol-1-yl)-1,1,3,3-tetramethyluronium hexafluorophosphate) and an additive selected from HOBt (1-hydroxybenztriazole), HOSu (N-hydroxysuccinimide) or HOAt (1-hydroxy-7-azabenzotriazole and common combinations thereof such as TBTU/HOBt or HBTU/HOAt.

In a preferred embodiment the coupling agent is selected from EDC (N-(3-dimethylaminopropyl)-N'-ethylcarbodiimide-hydrochloride) and HOSu (N-hydroxysuccinimide) as additive.

In case the GalNAc cluster is applied in the form of an alkali metal salt or an earth alkali metal salt the activation has to be performed in an acidic environment. Suitable acids are mineralic acids such as ortho-phosphoric acid or an organic acids such as methanesulfonic acid and a suitable polar aprotic solvent such as in N,N'-dimethyl formamide. The reaction temperatures can be selected between 10° C. and 40° C.

For the coupling the amine base usually is a tertiary amine, like triethylamine or N-ethyldiisopropylamine, pyridine derivatives such as 2,4,6-collidine or DABCO (1,4-Diazabicyclo[2.2.2]octane), but preferably N-ethyldiisopropylamine. The reaction takes place in a polar aprotic solvent like acetonitrile, dimethyl sulfoxide or tetrahydrofuran or mixtures thereof at reaction temperatures in the range of 20° C. and 70° C.

Alternatively n-propylphosphonic acid anhydride trimer (T3P) or (3-(diethoxy-phosphoryloxy)-1,2,3-benzo[d]triazine-4(3H)-one (DEPBT) is selected as coupling agent together with a tertiary amine base like triethylamine or N-ethyldiisopropylamine, but preferably with N-ethyldiisopropylamine Filtration of the reaction mixture provides GalNAc-cluster oligonucleotide conjugate containing filtrate which can be used in the subsequent purification step.

Step e):

Step e) requires purifying the GalNAc-cluster oligonucleotide conjugate

The purification of the GalNAc-cluster oligonucleotide conjugate obtained from the previous steps essentially comprises the steps chromatography, concentration and isolation. Chromatography and concentration steps can be applied repeatedly.

Suitable purification procedures comprise the sequence of the steps
  I. chromatography
  II. concentration
  III. isolation
or
  I. chromatography
  II. concentration
  III. chromatography
  IV. concentration
  V. isolation
or
  I. chromatography
  II. concentration
  III. isolation
  IV. chromatography
  V. concentration
  VI. isolation The purification procedure comprising the sequence I. to V. is preferred.

Even more preferred are purification procedures which comprise the sequence of the steps
  I. anion exchange chromatography or reversed phase chromatography
  II. tangential flow filtration
  III. lyophilization or spray drying
or
  I. anion exchange chromatography or reversed phase chromatography
  II. tangential flow filtration
  III. anion exchange chromatography or reversed phase chromatography
  IV. tangential flow filtration
  V. lyophilization or spray drying.

The purification methods mentioned above are common and well known to the skilled in the field of the present invention.

The term chromatography comprises the methods anion exchange chromatography or reversed phase chromatography and combinations thereof.

The anion-exchange chromatography is based on the competitive interaction of charged ions of the sample solution with the buffer medium employed. It can be carried out with conventional, commercially available anion-exchange resins, preferably those with trimethylammonium-functionalization. These phase materials can be obtained for example from GE Healthcare, Tosoh Bioscience, Bio-Rad or Merck. Particular good results have been achieved with the anion-exchange resin TSKgel Super Q-5PW (QAE), available from Tosoh Bioscience.

The reversed-phase chromatography can be carried out with traditional, commercially available phase materials such as a modified silica gel sorbents as stationary phase and suitable organic solvents such as acetonitrile and, if applicable, a buffer. Suitable modified silica gel type phase materials can be selected from Kromasil™C18, Kromasil™C8, YMC Triart C18 and YMC Triart C8. Particular good results have been achieved with the Triart Prep C8-S from YMC.

The term concentration comprises the methods tangential flow filtration or evaporation and combinations thereof.

In the tangential flow filtration or cross flow filtration the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate. The principles of tangential flow filtration is also used in nanofiltration, ultrafiltration, diafiltration and microfiltration processes. Suitable membranes are commercially available, for instance from Merck Millipore under the trade name Pellicon™. Suitable membranes have a molecular weight cut-off (MWCO) of ≤3 kDA. The Merck Millipore Pellicon 2 and 3 membranes with an MWCO of 1 kDA or 3 kDA respectively are preferred.

The term isolation comprises the methods lyophilization, precipitation, spray drying and evaporation. All these terms are well known to the skilled in the art.

In a non-limiting embodiment the oligonucleotide is selected from the group consisting of:

AM-C6*-5'-A*A*T*g*c*t*a*c*a*a*a*c*$^{Me}$C*$^{Me}$C*A-3'  (Compound 1)

AM-C6-5'-caG*$^{Me}$C*G*t*a*a*a*g*a*g*a*G*G-3'  (Compound 2)

AM-C6-5'-ca$^{Me}$C*$^{Me}$C*t*a*t*t*t*a*a*c*a*-t*c*A*G*A*$^{Me}$C-3'  (Compound 5)

AM-C6-5'-ca$^{Me}$C*T*A*a*t*t*g*t*a*g*t*-a*g*t*a*$^{Me}$C*T*$^{Me}$C-3'  (Compound 6)

wherein AM-C6 means a C6 amino linker; * stands for phosphorthioate bridges; A,G,T and $^{Me}$C (5-methyl cytosine) are LNA nucleoside monomers and a,t,c,g are DNA nucleoside monomers.

In a non-limiting embodiment, the GalNAc cluster oligonucleotide conjugate may be selected from the group consisting of:

GN2-AM-C6*-5'-A*A*T*g*c*t*a*c*a*a*a*c*$^{Me}$C*$^{Me}$C*A-3'  (Compound 3)

GN2-AM-C6-5'-caG*$^{Me}$C*G*t*a*a*a*g*a*g*a*G*G-3'  (Compound 4)

GN2-AM-C6-5'-ca$^{Me}$C*$^{Me}$C*t*a*t*t*t*a*a*c*a*-t*c*A*G*A*$^{Me}$C-3'  (Compound 7)

GN2-AM-C6-5'-ca$^{Me}$C*T*A*a*t*t*g*t*a*g*t*-a*g*t*a*T*M*T*$^{e}$C-3'  (Compound 8)

wherein AM-C6 means a C6 amino linker; * stands for phosphorthioate bridges; A,G,T and $^{Me}$C (5-methyl cytosine) are LNA nucleoside monomers and a,t,c,g are DNA nucleoside monomers and GN2 is the GalNAc cluster moiety which may occur in the form of the stereoisomers GN2a or GN2b, or mixtures thereof of the formula below, wherein R signifies the AM-C6-oligonucleotide tail.

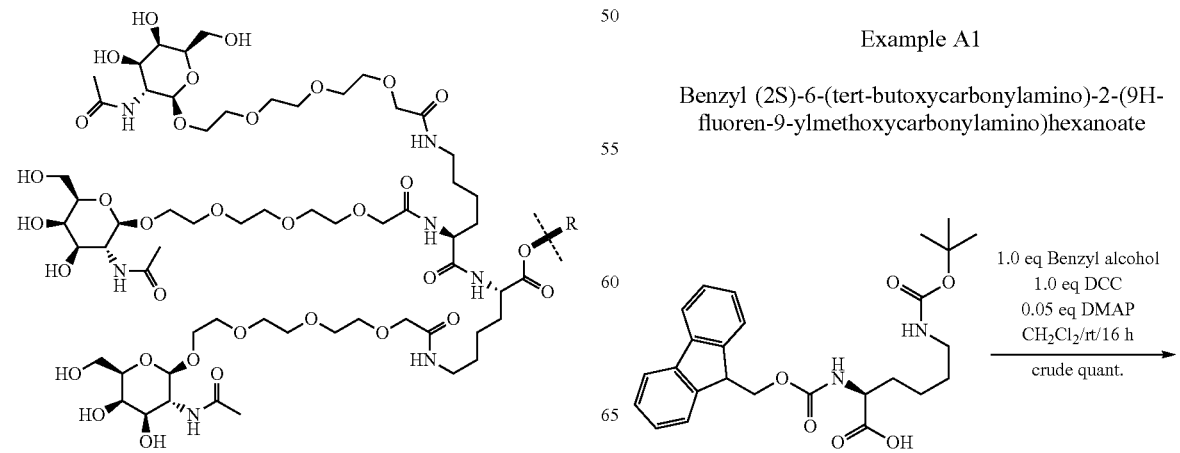

GN2a

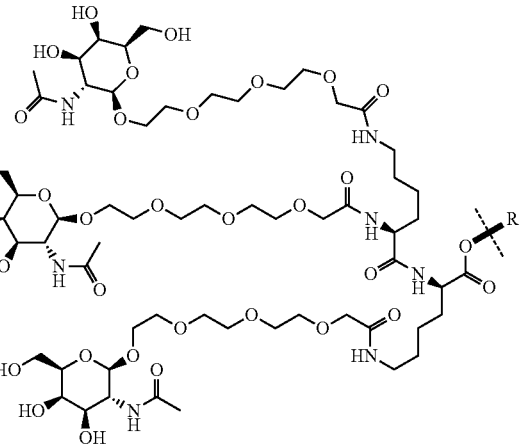

GN2b

The compounds disclosed herein have a nucleobase sequence selected from the group consisting of SEQ ID NO 1, 2, 3 and 4.

SEQ ID NO 1: aatgctacaaaaccccca (Examples 1A, 2A, 3A, 4A)

SEQ ID NO 2: cagcgtaaagagagg (Examples 1B, 2B, 3B, 4B1, 4B2,1C, 2C, 3C, 1D, 2D, 3D, 4C, 4D, 1E, 2E, 1F, 2F)

SEQ ID NO 3: cacctatttaacatcagac (Examples 1G, 1I, 1J, 2G, 2I, 2J, 3E, 3G, 4E1, 4E2, 4E3, 4E4, 5)

SEQ ID NO 4: cactaattgtagtagtactc (Examples 1H, 2H, 3F, 4F1, 4F2).

EXAMPLES

Abbreviations

AcOH acetic acid
DMAP 4-(dimethylamino)-pyridine
DMF N, N'-dimethylformamide
EtOH ethanol
MeOH methanol
rt room temperature
THF tetrahydrofuran
TBME tert.-butyl methyl ether
ACN acetonitrile Preparation of the GalNAc Cluster Compound Precursor Building Block A:

Example A1

Benzyl (2S)-6-(tert-butoxycarbonylamino)-2-(9H-fluoren-9-ylmethoxycarbonylamino)hexanoate

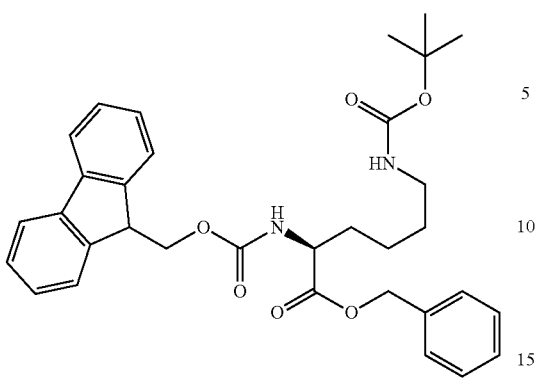

234.0 g (500.0 mmol) (2S)-6-(tert-butoxycarbo-nylamino)-2-(9H-fluoren-9-ylmethoxycarbonylamino) hexanoic acid was suspended in 500 ml dichloromethane, 62.0 ml (600 mmol, 1.2 eq) benzyl alcohol and 3.05 g DMAP (25.0 mmol, 0.05 eq) were added. The solution was cooled to 0-5° C. in the course of 40 min, a solution of 108.0 g (525.0 mmol, 1.05 eq) N,N'-dicyclohexyl carbodiimide in 500 ml dichloromethane, was added dropwise. The white suspension was stirred for 1 h at 0-5° C. and then for 15 h at room temperature. The suspension was filtered over a G3 glass filter, the white filter cake was washed portion-wise with total 250 ml dichloromethane. The filtrate was evaporated at 650-10 mbar/1 h to obtain a yellow oil, which was in dissolved in 2.0 L ethyl acetate, extracted with 2.0 L 0.5M hydrochloric acid, 2.0 L 1M NaHCO₃ and 1.0 L brine, the organic layer was evaporated to dryness at 40° C./150-10 mbar/5 h to obtain 291.1 g crude benzyl (2S)-6-(tert-butoxycarbonylamino)-2-(9H-fluoren-9-ylmethoxycarbo-nylamino) hexanoate as white solid in 104% yield and 96.4% purity (HPLC area-%; contains ca. 5% benzyl alcohol). The material was used in the next step without further purification. MS: m/z=459.22735 (M–boc+H)⁺.

Example A2

Benzyl (2S)-2-amino-6-(tert-butoxycarbonylamino)hexanoate methanesulfonic Acid Salt

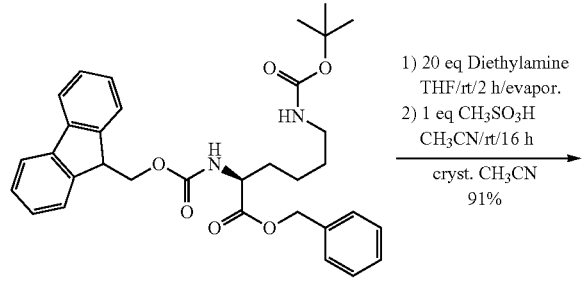

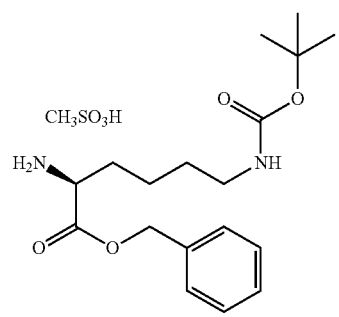

291.1 g Benzyl (500.0 mmol) (2S)-6-(tert-butoxycarbo-nylamino)-2-(9H-fluoren-9-ylmethoxycarbonylamino) hexanoate (HPLC purity; 95.8%; contains ca. 5% benzyl alcohol) were dissolved in 1.4 L THF at room temperature. Within 10 min, 1.04 L diethylamine (10.0 mol, 20 eq) were added, the light yellow solution was stirred for 2 h at room temperature and then evaporated at 40° C./200-10 mbar, 200 ml acetonitrile was added and evaporated again to efficiently remove diethylamine at 40° C./100-10 mbar/1 h. Finally, 268.1 g of a yellow oil was obtained, which was dissolved in 2.5 L acetonitrile, stirred for 10 min at room temperature. Insoluble particles were filtered over a glass fiber filter and washed with 500 ml acetonitrile. The filtrate was treated dropwise in the course of 10 min with 34.0 ml methane-sulfonic acid at 20° C.-25° C. The formed white suspension was stirred for 17 h at room temperature and filtered over a G3 glass filter. The filter cake was washed portion-wise with 500 ml acetonitrile. The white crystals were dried at 40° C./15 mbar/4 h to obtain 195.8 g benzyl (2S)-2-amino-6-(tert-butoxycarbonylamino)hexanoate methanesulfonic acid salt as white crystals in 91% yield (2 steps) and 99.3% purity (HPLC area-%). MS: m/z=337.2149 (M+H)⁺.

Example A3

Benzyl (2S)-2-[[(2S)-2,6-bis(tert-butoxycarbo-nylamino)hexanoyl]amino]-6-(tert-butoxycarbo-nylamino)hexanoate

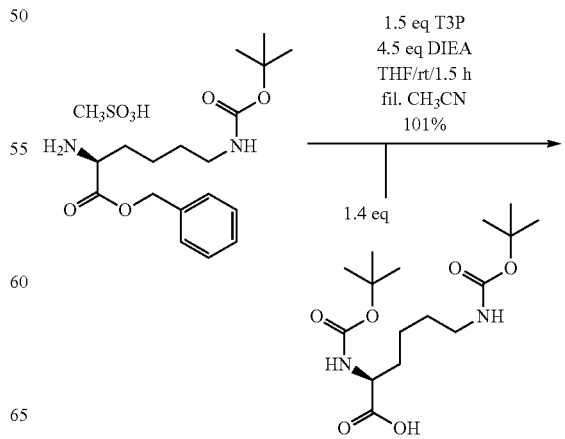

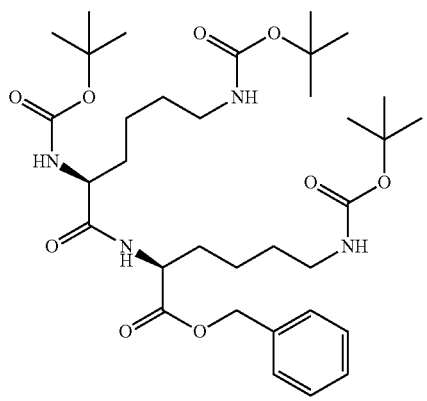

190.0 g (439.0 mmol) Benzyl (2S)-2-amino-6-(tert-butoxycarbonylamino)hexanoate methanesulfonic acid salt were suspended in 1.9 L THF at room temperature. 335 ml (1.98 mol, 4.5 eq) N-ethyldiisopropylamine were added whereby the temperature slightly decreased to 15° C. Next, 213 g (615 mmol, 1.4 eq) (S)-2,6-bis((tert-butoxycarbonyl)amino)hexanoic acid were added and the white suspension was stirred at room temperature for 20 min. 390 ml n-propylphosphonic acid anhydride (T3P as cyclic trimer 50% in ethyl acetate, 659 mmol, 1.5 eq) were added dropwise in the course of 20 min at 20-25° C. (cooled in a cool water bath). The resulting light yellow, cloudy solution was stirred at room temperature for 1.5 h, transferred to a separating funnel, diluted with 1.9 L TBME and extracted with 1.9 L water, 1.9 L 0.5M hydrochloric acid, 1.9 L0.5M NaOH, 1.9 L water and 1.9 L brine. The separated, still cloudy organic layer was filtered over a glass fiber filter, the filter was washed with 100 ml TBME and the combined filtrates were evaporated at 40° C./100 mbar/1 h, 1.0 L TBME (to aceotropic remove water) were added again and evaporated at 40° C./250-10 mbar/1 h to obtain crude 296.4 g as white solid residue.

The crude solid was treated with 500 ml acetonitrile and the cloudy solution was heated to 60-65° C. for 10 min. The mixture was cooled to 20-25° C., stirred for 10 min, filtered over a glass fiber filter and washed with 50 ml acetonitrile. The light yellow solution was evaporated at 40° C./100-10 mbar/4 h to obtain 295 g benzyl (2S)-2-[[(2S)-2,6-bis(tert-butoxycarbonylamino)hexanoyl]amino]-6-(tert-butoxycarbonylamino)hexanoate as off-white solid in a yield of 101% (HPLC purity: 100%, diastereomer purity (SS) 98.6%) which was used without further purification in the next step. MS: m/z=565.3741 (M-boc+H)+.

Example A4

Benzyl (2S)-6-amino-2-[[(2S)-2,6-diaminohexanoyl]amino]hexanoate tri-methanesulfonic Acid Salt

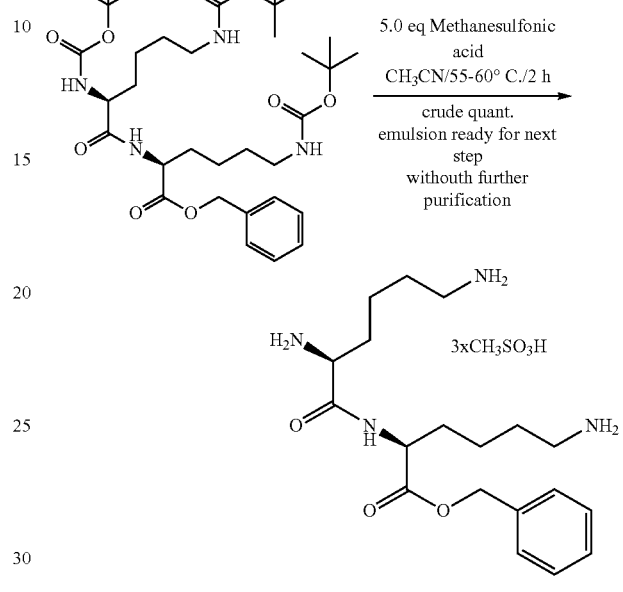

124.0 g (187 mmol) benzyl (2S)-2-[[(2S)-2,6-bis(tert-butoxycarbonylamino)hexanoyl]amino]-6-(tert-butoxycarbonylamino)hexanoate was suspended in 1.25 L acetonitrile. 61.0 ml (935.0 mmol, 5.0 eq) methanesulfonic acid was added at 20-25° C. in the course of 10 min (gas evolution). The resulting orange suspension was heated in 40 min to 55-60° C. and stirred for another 1 h at 55-60° C. The orange-red emulsion was cooled to room temperature (debocation was controlled by $^1$H-NMR) and used without further purification in the A+B assembly step, example 8. MS: m/z=365.2558 (M+H)+.

Building Block B:

Example B1a

Benzyl 2-[2-[2-(2-hydroxyethoxy)ethoxy]ethoxy]acetate

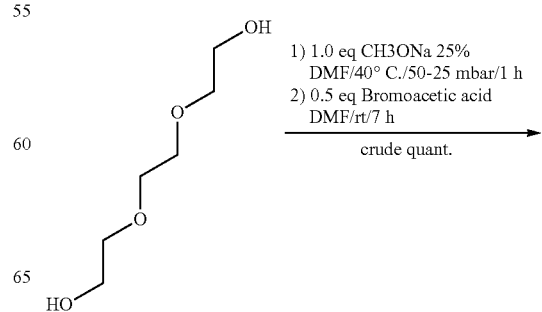

-continued

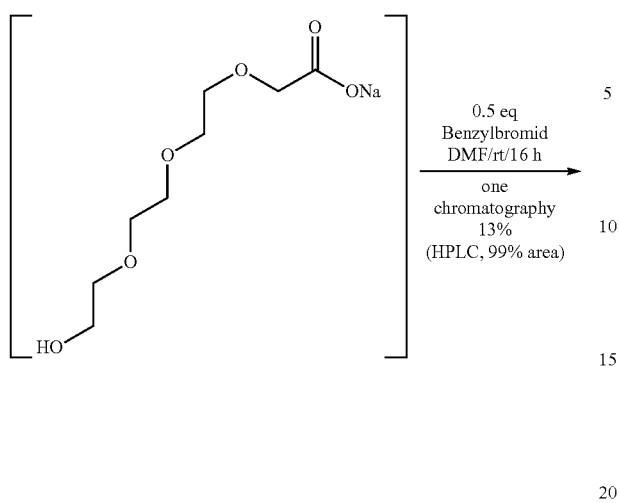

Example B1b

Benzyl 2-[2-[2-(2-hydroxyethoxy)ethoxy]ethoxy]acetate

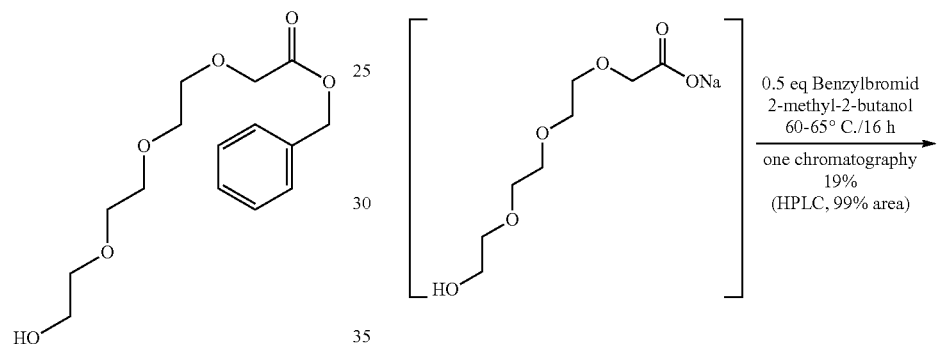

30.0 g (200.0 mmol), 2-[2-(2-Hydroxyethoxy)ethoxy]ethanol were dissolved in 50 ml DMF, at 20-25° C., then, 46.0 ml sodium methoxide 25% (200.0 mmol, 1.0 eq) in methanol were added. The formed solution was evaporated at 40° C./50 mbar/0.5 h (remove of 40 ml solvent), 50 ml DMF was added again and evaporated at 40° C./20 mbar/0.5 h (remove of 15 ml solvent), To the slightly jellylike suspension a solution of 13.9 g bromoacetic acid (100 mmol, 0.5 eq) in 50 ml DMF was added at 20-25° C. and the mixture was stirred for 6 h. 11.9 ml benzyl bromide (100 mmol, 0.5 eq) was added and the mixture stirred for another 16 h at 20-25° C. The reaction mixture was then treated with 200 ml brine and extracted with 200 ml TBME. The separated TBME layer was extracted with 200 ml brine, the separated TBME layer was then dried with anhydrous sodium sulfate, filtered and evaporated at 40° C./300-10 mbar/1 h to obtain crude 23.9 g benzyl 2-[2-[2-(2-hydroxyethoxy)ethoxy]ethoxy]acetate.

After chromatography (600 g silica 60 (0.063-0.2 mm), mobile phase: ethyl acetate) a total of 7.85 g benzyl 2-[2-[2-(2-hydroxyethoxy)ethoxy]ethoxy]acetate as colorless oil was isolated in 13% yield and 99.0% purity (HPLC area-%). MS: m/z=299.1517 (M+H)$^+$.

11.2 g potassium tert.-butylate (100.0 mmol, 0.5 eq) was suspended in 70 ml 2-methyl-2-butanol (light exothermic 35° C.), then 30.0 g (200.0 mmol) 2-[2-(2-Hydroxyethoxy)ethoxy]ethanol were added dropwise in the course of 5 min. the dropping funnel were rinsed with 10 ml 2-methyl-2-butanol (temp. increase to 45° C.), the solution was heated to 60-65° C., 11.6 g (100 mmol, 0.5 eq) sodium chloroacetate were added and stirred for 16 h at 60-65° C., then 11.9 ml benzyl bromide (100 mmol, 0.5 eq) were added and the mixture stirred for another 16 h at 60-65° C. The reaction mixture was cooled to rt, then treated with 50 ml water and extracted with 80 ml TBME and 40 ml TBME. The combined TBME layer was washed with 50 ml half saturated brine, the organic layer were evaporated at 40° C./300-10 mbar/1 h to obtain crude 27.0 g benzyl 2-[2-[2-(2-hydroxyethoxy)ethoxy]ethoxy]acetate.

After chromatography (270 g silica 60 (0.063-0.2 mm), mobile phase: start with ethyl acetate/n-heptane 1/1, when pure product are visible, mobile phase were changed to 100% ethyl acetate, total 11.4 g benzyl 2-[2-[2-(2-hydroxyethoxy)ethoxy]ethoxy]acetate as nearby colorless oil was isolated in 19% yield (38% from sodium chloroacetate) and 99.0% purity (HPLC area-%)

Example B2

Benzyl 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetate 268.0 g Benzyl 2-(2-(2-(2-hydroxyethoxy)ethoxy)ethoxy)acetate (900 mol) were dissolved in 2.4 L dichloromethane. 385.0 g (2S,3R,4R,5R,6R)-3-acetamido-6-(acetoxymethyl)tetrahydro-2H-pyran-2,4,5-triyl triacetate (990 mmol, 1.1 eq) and 12.0 ml trifluoromethanesulfonic acid (135 mmol, 0.15 eq) were added. The suspension was heated to reflux with a dean-stark separator (50 ml, to remove AcOH). After 1 h, 4.50 ml trifluoromethanesulfonic acid (50.7 mmol, 0.05 eq) and 50 ml dichloromethane were added to the orange suspension, the solvent (50 ml) from the dean-stark separator was discharged. Every half hour this procedure was repeated, total 6 times (3 h). After a total of 4.5 h, the red solution was cooled to 10-15° C. and added within 30 min at 20-25° C. to a solution of 1.8 L 1M sodium hydrogen carbonate (1.8 mol, 2.0 eq) ($CO_2$ evolution, pH 7-8). The yellow organic layer was separated and evaporated at 40° C./600-10 mbar/3 h to obtain 585.4 g of crude benzyl 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetate as yellow oil (HPLC purity: 87%). The crude product was dissolved in 700 ml acetone and charged to a preloaded silica column (3.0 kg silica 60; 0.063-0.2 mm). The chromatography was conducted using n-heptane/acetone as mobile phase (gradient from 5:1 to 1:2). The combined collected fractions were evaporated at 40° C./600-10 mbar and dried at 20-25° C./0.3 mbar/3 h to obtain 465.0 g benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate as yellow oil in 83% yield and 100% purity (HPLC area-%). MS: m/z=628.2627 (M+H)$^+$.

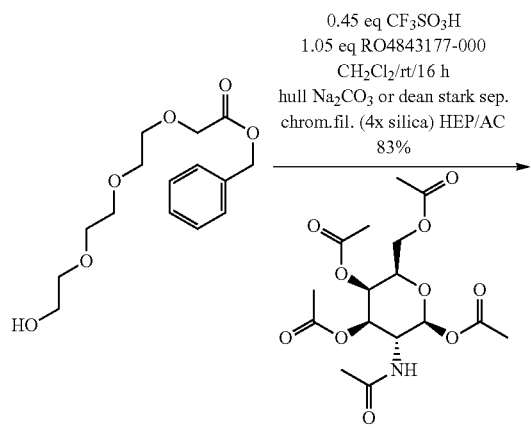

Example B3

2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic Acid

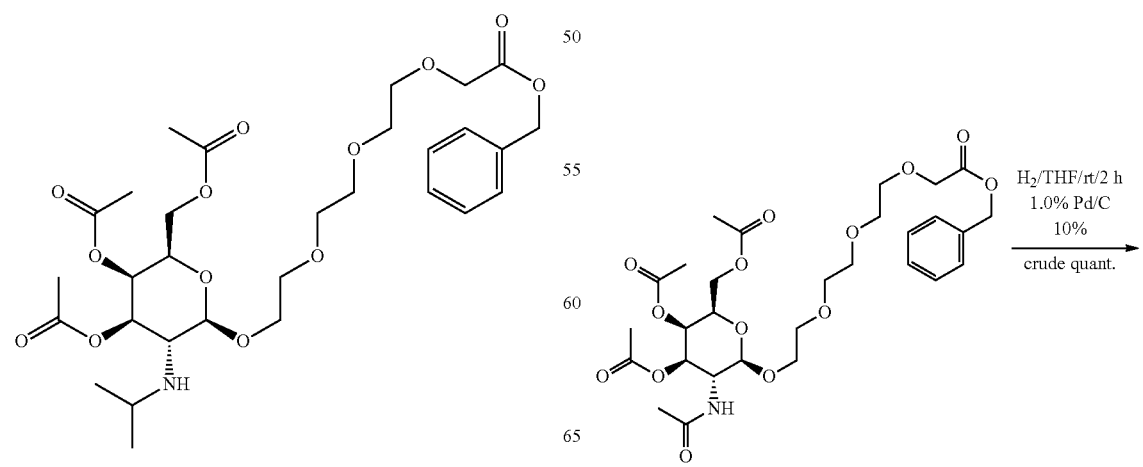

-continued

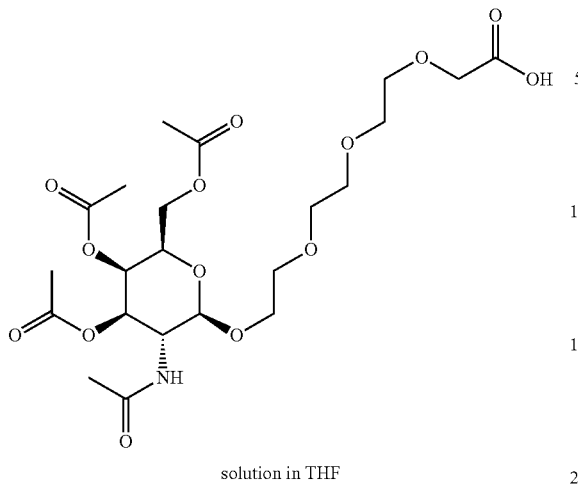

solution in THF

Under argon atmosphere, 456.0 g Benzyl 2-[2-[2-[2-[(2R,3R,4R,5R,6R)-3-acetamido-4,5-diacetoxy-6-(acetoxymethyl)tetrahydro-pyran-2-yl]oxyethoxy]ethoxy]ethoxy]acetate (727 mmol) were dissolved in 1.4 L THF. 4.56 g Pd/C 10% were added and the argon atmosphere was replaced with hydrogen (1 bar). The black suspension was hydrogenated at 20-25° C. for 2 h. The hydrogen atmosphere was replaced with argon, the black suspension was filtered and the filter cake was washed portion-wise with total of 400 ml THF. The colorless filtrate (HPLC purity: 71% and 27% toluene) was used without any purification in the A+B assembly step, example C1. MS: m/z=538.2191 (M+H)$^+$.

Assembly of Building Block A and B

Example C1

Benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate

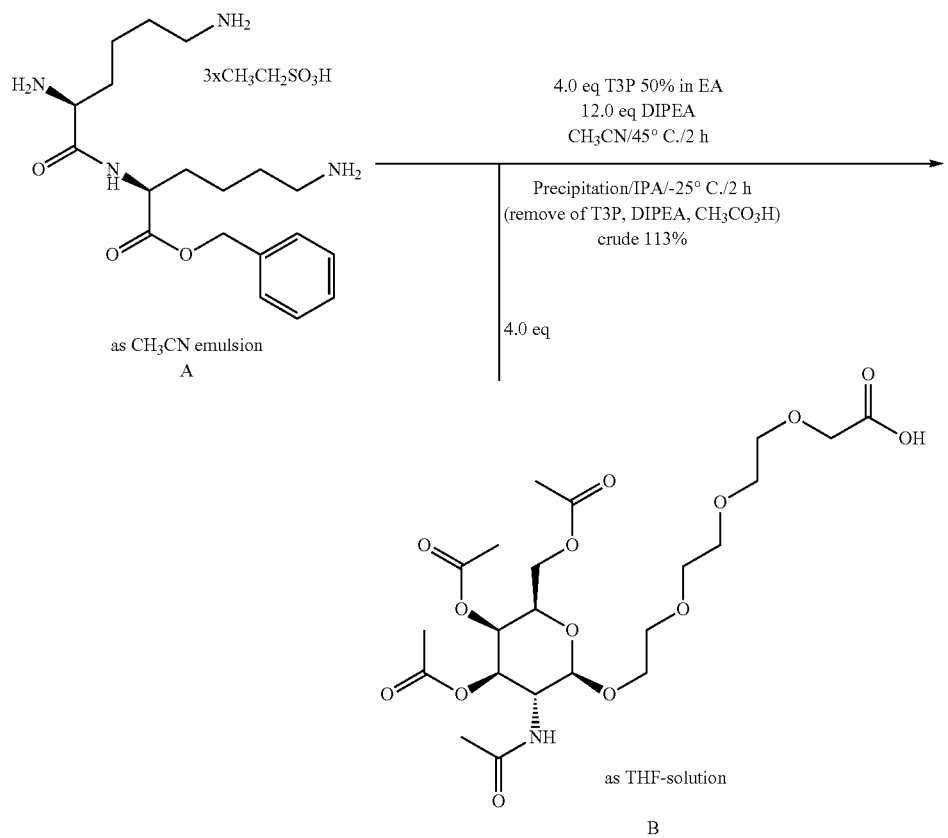

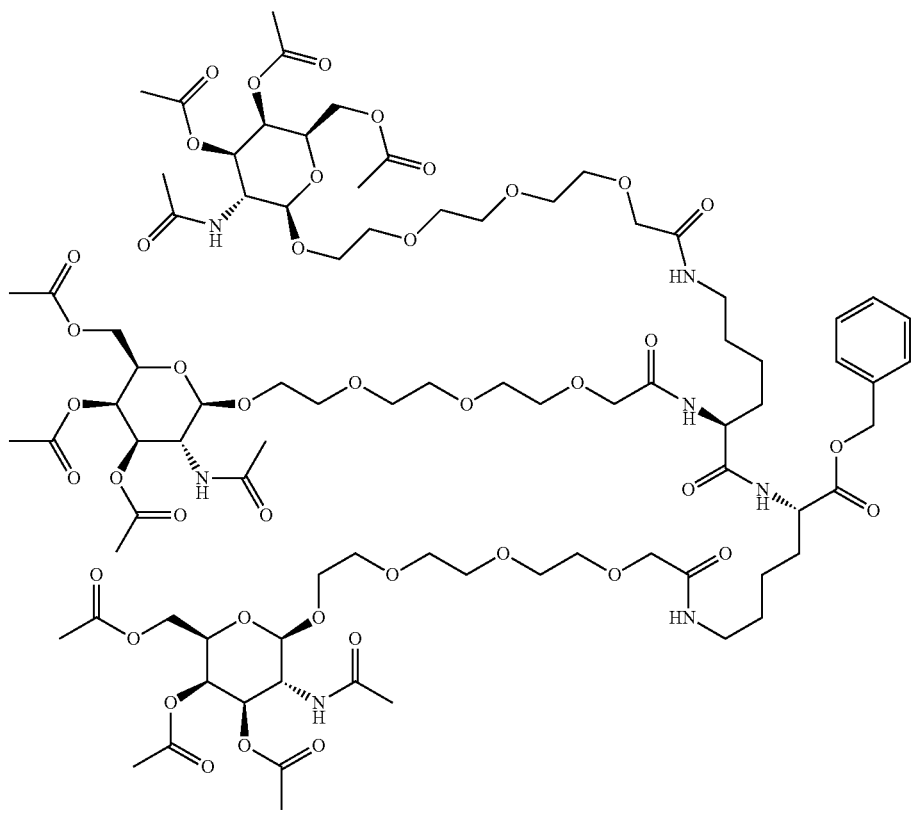

The red-orange solution (~1.4 L) of benzyl (2S)-6-amino-2-[[(2S)-2,6-diaminohexanoyl]amino]hexanoate trimethanesulfonate (180.0 mmol) from Example 4 was diluted with 3.60 L acetonitrile. At 20-25° C., 365.0 ml N-ethyldiisopropylamine (2.16 mol, 12.0 eq) were added within 5 min. To the formed sticky slurry, a solution (~2.25 L) of 2-[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid (720 mmol, 4.0 eq) from Example B3 was added at 20-25° C. in within 10 min, whereby the temperature slightly increased to 40° C. At 45-50° C., a solution of 425 ml n-propylphosphonic acid anhydride (T3P, trimer 50% in ethyl acetate, 720 mmol, 4.0 eq) was added within 10 min. The reaction solution was stirred for 1 h at 45-50° C. The light yellow solution was cooled to 20-25° C. and evaporated at 40° C./10 mbar/6 h to obtain crude 1.06 kg benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 24.1%). The crude product was precipitated in three portions to remove methanesulfonic acid N-ethyldiisopropylamine and residual T3P. 353 g crude product was dissolved in 7.0 L 2-propanol, cooled in 1 h to −25° C., stirred for 1 h at −25° C., filtered over a precooled (−25° C.) G3-glass-filter (no rinse), a part from the precipitated product deposited on the glass-wall from the reactor. All precipitates were dissolved portion-wise from the filter and glass-wall with a total of 1.0 L THF. The combined solutions were evaporated at 40° C./20 mbar/6 h to obtain 390.0 g benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 71.9%), which was used without further purification in the next step. MS: m/z=1923.8438 (M+H)+

33
Example C2
Sodium;(2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]
34
amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate
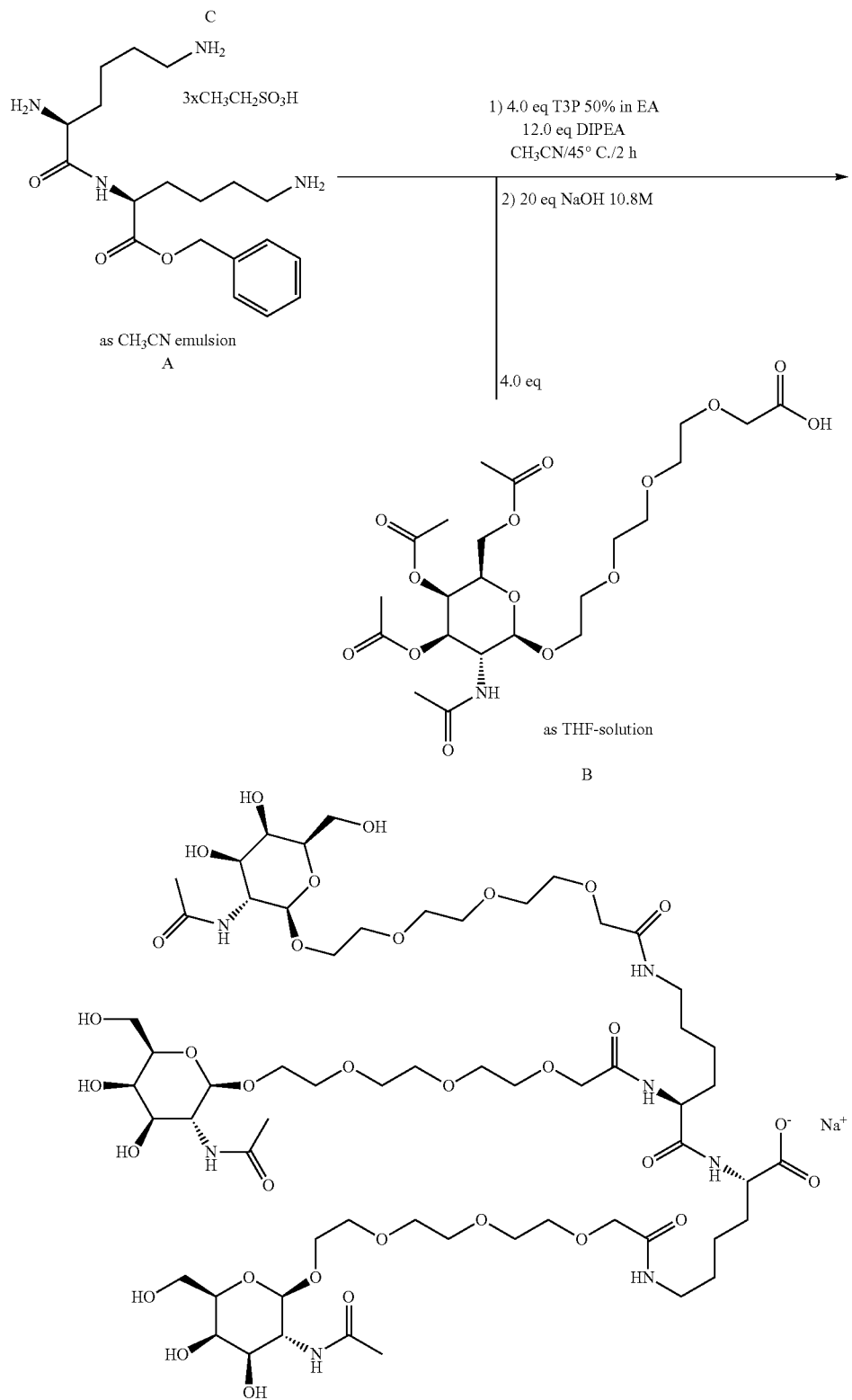

The red-orange solution (~95 ml) of benzyl (2S)-6-amino-2-[[(2S)-2,6-diaminohexanoyl]amino]hexanoate tri-methanesulfonate (12.2 mmol) was diluted with 240 ml acetonitrile. At 20-25° C., 30.0 ml N-ethyldiisopropylamine (2.16 mol, 14.5 eq) were added within 5 min. To the formed sticky slurry, a solution (~150 ml) of 2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetic acid (48.8 mmol, 4.0 eq) was added at 20-25° C. in within 10 min, whereby the temperature slightly increased to 40° C. At 45-50° C., a solution of 28.8 ml n-propylphosphonic acid anhydride (T3P, trimer 50% in ethyl acetate, 48.8 mmol, 4.0 eq) was added within 10 min. The reaction solution was stirred for 1 h at 45-50° C. The light yellow solution was cooled to 20-25° C. and evaporated at 40° C./10 mbar/6 h to obtain crude 73.6 g benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]hexanoyl]amino]hexanoate (HPLC purity: 32% area).

68.0 g (11.0 mmol) of the crude product was dissolved in 340 ml methanol 20.0 ml (220 mmol, 20 eq) NaOH 10.8M was added to the light yellow solution, the temperature increased to 32° C., the reaction mixture was stirred for 2.5 h at rt, whereby a suspension was formed (pH 12.0). The suspension was filtered and the filter cake was washed with 100.0 ml methanol, the filtrate was evaporated at 40° C./250-10 mbar/2 h to obtain 41.5 g sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]hexanoyl]amino]hexanoate, which was then purified by preparative reversed phase chromatography, conditions see experiment C3.

Example C3

Sodium;(2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[2-[(2R,3R,4R,5R,6R)-3-acetamido-4,5-dihydroxy-6-(hydroxymethyl)tetrahydropyran-2-yl] oxyethoxy] ethoxy] ethoxy] acetyl]amino]hexanoyl]amino]hexanoate

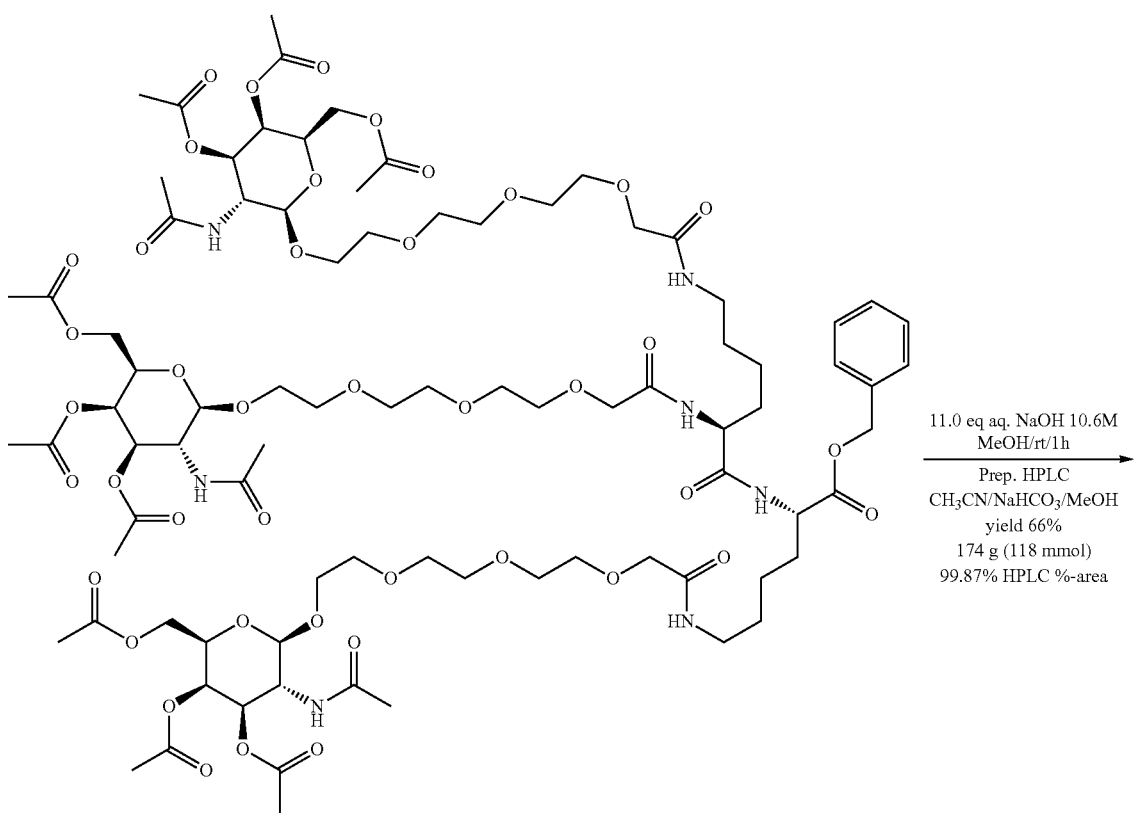

11.0 eq aq. NaOH 10.6M
MeOH/rt/1h

Prep. HPLC
CH₃CN/NaHCO₃/MeOH
yield 66%
174 g (118 mmol)
99.87% HPLC %-area

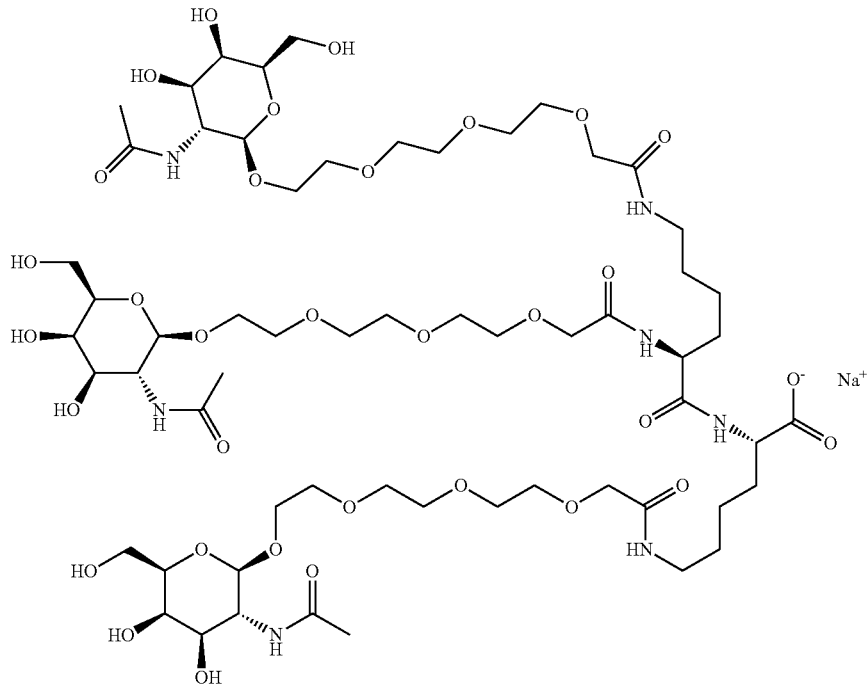

378.0 g (197.0 mmol, crude) Benzyl (2S)-6-[[2-[2-[2-[2-[(2R,3R,4R,5R,6R)-3-acetamido-4,5-diacetoxy-6-(acetoxymethyl)tetrahydropyran-2-yl]oxyethoxy]ethoxy]ethoxy]acetyl]amino]-2-[[(2S)-2,6-bis[[2-[2-[2-[(2R,3R,4R,5R,6R)-3-acetamido-4,5-diacetoxy-6-(acetoxymethyl)tetrahydropyran-2-yl]oxyethoxy]ethoxy]acetyl]amino]hexanoyl]amino]hexanoate was dissolved in 1.9 L methanol. Within 10 min, 200.0 mL 10.8 M sodium hydroxide solution (2.16 mol, 11.0 eq) were added at 20-25° C. Thereby the temperature increased to 31° C. The light yellow solution was stirred for 2 h at 20-25° C. (pH 13.4), then 80.0 mL 5M ammonium chloride solution were added (pH 10.7). The light yellow solution was then evaporated at 20-25° C./100-20 mbar/5 h and dried at 20-0.5 mbar/1 h to obtain crude 543 g sodium (2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]ethoxy]acetyl]amino]-2-[[(2S)-2,6-bis[[2-[2-[2-[(2R,3R,4R,5R,6R)-3-acetamido-4,5-dihydroxy-6-(hydroxymethyl)tetrahydropyran-2-yl]oxyethoxy]ethoxy]acetyl]amino]hexanoyl]amino]hexanoate (HPLC purity: 40.1%), which was then purified by preparative reversed phase chromatography.

Column: Triart C18-120 26×15 cm; 10 um;
Mobile phase: A: 2 mM NaHCO₃/B: Acetonitrile;
Gradient:

| Minutes | A | B | Flow(ml/Min) |
|---|---|---|---|
| 0 | 94 | 6 | 700 |
| 2 | 94 | 6 | 700 |
| 20 | 88 | 12 | 700 |
| 20.1 | 10 | 90 | 750 |
| 26 | 10 | 90 | 750 |
| 26.1 | 94 | 6 | 700 |
| 36 | 94 | 6 | 700 |

Thermostatization: room temperature

Detection: 220 nm

Solution: 543 g dissolved in 4500 ml 2 mM NaHCO₃ and filtered (GF5)(=5000 ml (109 mg/ml)

Sample solution/Injection: Per run 200 ml sample=21.8 g (25 runs)

Concentration: The combined fractions (46 L) were diluted with 110 L water, this solution were pumped in 3 portions to a RP C18 column and washed with water/MeOH 98/2, then with MeOH eluted and concentrated on a rotary evaporator to obtain 1.18 kg methanolic solution. A quarter of the 1.18 kg methanolic solution of the preparative HPLC purification step, i.e. 295 g were evaporated at 40° C./20 mbar/1 h and then at 20-25° C./0.35 mbar/14 h to dryness to obtain 43.5 g sodium;(2S)-6-[[2-[2-[2-[2-[(2R,3R,4R,5R,6R)-3-acetamido-4,5-dihydroxy-6-(hydroxymethyl)tetrahydropyran-2-yl]oxyethoxy]ethoxy]acetyl]amino]-2-[[(2S)-2,6-bis[[2-[2-[2-[(2R,3R,4R,5R,6R)-3-acetamido-4,5-dihydroxy-6-(hydroxymethyl)tetrahydropyran-2-yl]oxyethoxy]ethoxy]acetyl]amino]hexanoyl]amino]hexanoate as amorphous white powder, 99.88% HPLC purity. The remaining three-quarters of the above solution (885 g) were used in the next step. MS: m/z=1452.684 (M−H)⁻.

Preparation of the GalNAc Cluster Oligonucleotide Conjugate

Example 1A

Preparation of $CF_3CO$-AM-C6*-5'$A^{(bz)}$*$A^{(bz)}$* $T$*$g^{(ibu)}$*$c^{(bz)}$*$t$*$a^{(bz)}$$c^{(bz)}$*$a^{(bz)}$*$a^{(bz)}$*$a^{(bz)}$*$a^{(bz)}$* $c^{(bz)}$*$^{Me}C^{(bz)}$*$^{Me}C^{(bz)}$*$A^{(bz)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; $CF_3CO$=TFA=trifluoroacetyl; bz=benzoyl; ibu=isobutyryl The title compound was produced by standard phosphoramidite chemistry on solid phase at a scale of 1.60 mmol using an AKTA Oligopilot 100 (GE Healthcare, Freiburg, Germany and Primer Support 5G Unylinker 350 (GE Healthcare, Freiburg, Germany). Oligonucleotides containing LNA, i.e. 2'-$OCH_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 2.0 eq of the DNA/LNA-phosphoramidites and 3.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A, B1, B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2A.

Standard Reagent Solutions

| | |
|---|---|
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1B

Preparation of $CF_3CO$-AM-C6-5'$c^{(bz)}$$a^{(bz)}$ $G^{(dmf)}$*$^{Me}C^{(bz)}$*$G^{(dmf)}$*$t$*$a^{(bz)}$*$a^{(bz)}$*$a^{(bz)}$*$g^{(ibu)}$*$a^{(bz)}$* $g^{(ibu)}$*$a^{(bz)}$*$G^{(dmf)}$*$G^{(dmf)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; $CF_3CO$=TFA=trifluoroacetyl; bz=benzoyl; ibu=isobutyryl; dmf=dimethylformamidine The title compound was produced by standard phosphoramidite chemistry on solid phase at a scale of 1.90 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-$OCH_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2B.

Standard Reagent Solutions

| | |
|---|---|
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1C

Preparation of $CF_3CO$-AM-C6-5' $c^{(bz)}$$a^{(bz)}$$G^{(ibu)}$ *$^{Me}C^{(bz)}$*$G^{(ibu)}$*$t$*$a^{(bz)}$*$a^{(bz)}$*$a^{(bz)}$*$g^{(ibu)}$*$a^{(bz)}$* $g^{(ibu)}$ *$a^{(bz)}$*$G^{(ibu)}$*$G^{(ibu)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; $CF_3CO$=TFA=trifluoroacetyl; bz=benzoyl; ibu=isobutyryl; dmf=dimethylformamidine The title compound was produced by standard phosphoramidite chemistry on solid phase at a scale of 1.90 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-$OCH_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A,B1,B2, Oxidizer, DEA wash, were commercially available (Sigma-Aldrich, Merck Millipore, EMP Biotech;

see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2C.
Standard Reagent Solutions

| | |
|---|---|
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1D

Preparation of CF$_3$CO-AM-C6-5' c$^{(bz)}$a$^{(bz)}$G$^{(dmf)}$*$^{Me}$C$^{(bz)}$*G$^{(dmf)}$*t*a$^{(bz)}$*a$^{(bz)}$*a$^{(bz)}$*g$^{(ibu)}$*a$^{(bz)}$*g$^{(ibu)}$*a$^{(bz)}$*G$^{(dmf)}$*G$^{(dmf)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 1.60 mmol using an AKTA Oligopilot 100 (GE Healthcare, Freiburg, Germany and Primer Support 5G Unylinker 350 (GE Healthcare, Freiburg, Germany). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 2.0 eq of the phosphoramidites and 3.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2D.
Standard Reagent Solutions

| | |
|---|---|
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1E

Preparation of CF$_3$CO-AM-C6-5' c$^{(bz)}$a$^{(bz)}$G$^{(dmf)}$*$^{Me}$C$^{(bz)}$*G$^{(dmf)}$*t*a$^{(bz)}$*a$^{(bz)}$*a$^{(bz)}$*g$^{(ibu)}$*a$^{(bz)}$*g$^{(ibu)}$*a$^{(bz)}$*G$^{(dmf)}$*G$^{(dmf)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 0.20 mmol using an AKTA Oligopilot 100 (GE Healthcare, Freiburg, Germany and Primer Support Unylinker (Kinovate Nittophase®HL UnyLinker™400, USA. Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the phosphoramidites and 2.0 eq TFA-aminolinker-phosphoramidite per coupling were employed. Phosphorothiolation reagent (PADS), Bis-(phenylacetyl)-disulfid (ABCR, AB180887) was used as a 0.2M solution in anhydrous acetonitrile/3-picoline 1/1. All other standard reagent solution (DCA-debloc, BTT, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2E.
Standard Reagent Solutions

| | |
|---|---|
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1F

Preparation of CF$_3$CO-AM-C6-5' c$^{(bz)}$a$^{(bz)}$G$^{(dmf)}$*$^{Me}$C$^{(bz)}$*G$^{(dmf)}$*t*a$^{(bz)}$*a$^{(bz)}$*a$^{(bz)}$*g$^{(ibu)}$*a$^{(bz)}$*g$^{(ibu)}$*a$^{(bz)}$*G$^{(dmf)}$*G$^{(dmf)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 0.20 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, DCI, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2F.

Standard Reagent Solutions

| DCA-deblock | 3% Dichloroacetic acid in toluene (v/v) |
|---|---|
| DCI activator | 0.25M 4,5-Dicyanoimidazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1G

Preparation of CF$_3$CO-AM-C6-5'-c$^{(bz)}$a$^{(bz)Me}$C$^{(bz)}$*$^{Me}$C$^{(bz)}$*t*a$^{(bz)}$*t*t*t*a$^{(bz)}$*a$^{(bz)}$*c$^{(bz)}$*a$^{(bz)}$-t*c$^{(bz)}$*A$^{(bz)}$*G$^{(dmf)}$*A$^{(bz)}$*$^{Me}$C$^{(bz)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 1.90 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2G.

Standard Reagent Solutions

| DCA-deblock | 3% Dichloroacetic acid in toluene (v/v) |
|---|---|
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1H

Preparation of CF$_3$CO-AM-C6-5'-c$^{(bz)}$a$^{(bz)Me}$C$^{(bz)}$*T*A$^{(bz)}$*a$^{(bz)}$*t*t*g$^{(ibu)}$*t*a$^{(bz)}$*g$^{(ibu)}$*t*-a$^{(bz)}$*g$^{(ibu)}$*t*a$^{(bz)}$*$^{Me}$C$^{(bz)}$*T*$^{Me}$C$^{(bz)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 1.90 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A, B1, B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2H.

Standard Reagent Solutions

| DCA-deblock | 3% Dichloroacetic acid in toluene (v/v) |
|---|---|
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1I

Preparation of CF$_3$CO-AM-C6-5'-c$^{(bz)}$a$^{(bz)Me}$C$^{(bz)}$*$^{Me}$C$^{(bz)}$*t*a$^{(bz)}$*t*t*a$^{(bz)}$*a$^{(bz)}$*c$^{(bz)}$*a$^{(bz)}$*-t*c$^{(bz)}$*A$^{(bz)}$*G$^{(dmf)}$*A$^{(bz)}$*$^{Me}$C$^{(bz)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 0.2 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, Activator 42, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2I.

Standard Reagent Solutions

| | |
|---|---|
| DCA-deblock | 3% Dichloroacetic acid in toluene (v/v) |
| Activator 42 | 0.3M 5-(3,5-bis(trifluoromethyl)phenyl)-1H-tetrazole in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 1J

Preparation of CF$_3$CO-AM-C6-5'-c$^{(bz)}$a$^{(bz)Me}$C$^{(bz)}$*$^{Me}$C$^{(bz)}$*t*a$^{(bz)}$*t*t*a$^{(bz)}$*a$^{(bz)}$*c$^{(bz)}$*a$^{(bz)}$*-t*c$^{(bz)}$*A$^{(bz)}$*G$^{(dmf)}$*A$^{(bz)}$*$^{Me}$C$^{(bz)}$-3'-UnyLinker as its Diethylamine Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 1.90 mmol using an AKTA Oligopilot 100 (GE Healthcare, Freiburg, Germany and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, DCI, Cap A,B1,B2, Oxidizer, DEA wash, were commercially available (Sigma-Aldrich, Merck Millipore, EMP Biotech; see details below). Deprotection of 2-cyanoethyl-groupe was achieved by methods known as DEA-wash, to obtain crude protected polymer-support bonded Unylinker-LNA-oligo-nucleotide as diethylamine salt. The thereby obtained title compound was used without further operation in the experiment Example 2J.

Standard Reagent Solutions

| | |
|---|---|
| DCA-deblock | 3% Dichloroacetic acid in toluene (v/v) |
| DCI activator | 0.7M dicyanoimidazole in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer 0.05M | Water/pyridine/iodine 10/90/1.27 (v/v/w) |
| DEA wash | 20% Diethylamine in acetonitrile (v/v) |

Example 2A

Preparation of AM-C6*-5'-A*A*T*g*c*t*a*c*a*a*a*c*$^{Me}$C*$^{Me}$C*A-3' as its Sodium Salt The crude polymer-support bonded Unylinker-LNA-oligo-nucleotide as its diethylamine salt from Example 1A was treated with 180 ml conc. aq. ammonium hydroxide solution 30-32%. The suspension was stirred at 60° C. for 10 hour in a pressure stable closed flask. The suspension was filtered over a glass fiber filter and washed with 60 ml water. The yellow filtrate was evaporated at 40° C./300-10 mbar/2 h to obtain ~10.5 g crude oligo as ammonium salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5455.6. A total of 13 analogously prepared 1.6 mmol batches were combined with the above's one (total new batch size: 22.4 mmol) and dissolved in 750 ml water in one round bottom flask. The yellow solution were treated with 52.0 ml 10.8M NaOH (561.6 mmol) was added (pH 10) and the solution was evaporated at 40° C./100-10 mbar/2 h, the residue was treated with 100 ml water and concentrated in vacuo 40° C./100-10 mbar, this procedure was repeated total four times (the fourth distillate has a pH of 7.0). The oily residue was treated with 100 ml 2-methyl-2-butanol and evaporated at 40° C./50-10 mbar/2 h (azeotropic remove of water) to obtain 160 g as yellow solid. The crude product was suspended in 800 ml ethanol and warmed to 40-45° C. for 15 min, the yellow suspension was stirred for 1 h at 20-25° C. The suspension was filtered (remove of benzamide, isobutyrylamide, trifluoroacetamide and other by-products) and the filter cake was washed portion wise with 160 ml ethanol. The product was dried at 40-45° C./10 mbar/3 h to obtain 130.5 g of AM-C6*-5'-A*A*T*g*c*t*a*c*a*a*a*c*$^{Me}$C*$^{Me}$C*A-3' as its Sodium Salt as high density yellow powder with a LC-purity of 75.6% area (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5455.6. The product was used without further purification in the experiment Example 3A).

Example 2B

Preparation of AM-C6-5'-caG*$^{Me}$C*G*t*a*a*a*g*a*g*a*G*G-3' as its Sodium Salt The crude polymer-support bonded Unylinker-LNA-oligo-nucleotide as its diethylamine salt from Example 1B was treated with 180 ml conc. aq. ammonium hydroxide solution 30-32%. The suspension was stirred at 60° C. for 10 hour in a pressure stable closed flask. The suspension was filtered over a glass fiber filter and washed with 60 ml water. The yellow filtrate was evaporated at 40° C./300-10 mbar/2 h to obtain ~10.5 g crude oligo as ammonium salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5197.6. A total of 25 analogously prepared 1.9 mmol batches were combined with the above's one (total new batch size: 47.5 mmol) and dissolved in 1200 ml water in one round bottom flask. The orange solution were treated with 68.0 ml 10.8M NaOH (734.4 mmol, 15.5 eq, pH 10) and the solution was concentrated at 40° C./200-50 mbar to obtain ~600 g crude solution which was treated with 200 ml water and the same volume were destilled off in vacuo 40° C./50 mbar, this procedure were repeated total ten times (total 2000 ml water were destilled off, the 10th distillate has a pH of 7.0, all ammonia were removed). The obtained orange aqueous solution of 855 g, which contain in maximum 47.5 mmol product AM-C6-5'-caG*$^{Me}$C*G*t*a*a*a*g*a*g*a*G*G-3' as its Sodium Salt, were used without further purification in experiment Example 3B. 2×20 analogously prepared 1.9 mmol batches (2×38.0 mmol) were work up with the same procedure, total 123.5 mmol.

Example 2C

Preparation of AM-C6-5'-caG*$^{Me}$C*G*t*a*a*a*g*a*g*a*G*G-3' as its Sodium Salt The title compound was produced in analogy to Example 2B starting from material ex Example 1C. The obtained yellow aqueous solution of 148 g, which contain in maximum 1.9 mmol product, AM-C6-5'-caG*$^{Me}$C*G*t*a*a*a*g*a*g*a*G*G-3' as its sodium salt were used without further purification in the experiment Example 3C. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5197.6

Example 2D

Preparation of AM-C6-5'-caG*$^{Me}$C*G*t*a*a*a*g*a*g*a*G*G-3' as its Sodium Salt The crude polymer-support bonded Unylinker-LNA-oligo-nucleotide as its diethylamine salt from Example 1C was treated with 180 ml conc. aq. ammonium hydroxide solution 30-32%. The suspension was stirred at 60° C. for 10 hour in a pressure stable closed flask. The suspension was filtered over a glass fiber filter and washed with 60 ml water/ethanol 3/1. The yellow filtrate was evaporated at 40° C./300-10 mbar/2 h to obtain ~10.5 g crude oligo as ammonium salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5197.6. The residue 10.2 g (1.6 mmol) was dissolved in 250 ml water in one round bottom flask. The yellow solution were treated with 2.22 ml 10.8M NaOH (24 mmol, 15 eq, pH 10) and the solution was evaporated at 40° C./200-50 mbar to obtain a yellow oil which was treated two times with 10 ml water and the same volume were destilled off in vacuo 40° C./50-10 mbar (2. destillate pH 7.0 all ammonia were removed), The oily residue was treated with 30 ml 2-methyl-2-butanol and evaporated at 40° C./10 mbar to obtain crude 9.82 g as yellow solid (contain all cleaved protecting groups) AM-C6-5'-caG*$^{Me}$C*G*t*a*a*a*g*a*g*a*G*G-3' as its sodium salt, were used without further purification in the experiment Example 3D.

Example 2E

Preparation of AM-C6-5'-caG*$^{Me}$C*G*t*a*a*a*g*a*g*a*G*G-3' as its Sodium Salt The crude polymer-support bonded Unylinker-LNA-oligo-nucleotide as its diethylamine salt from Example 1E was treated with 25.0 ml conc. aq. ammonium hydroxide solution 30-32%. The suspension was stirred at 60° C. for 10 hour in a pressure stable closed flask. The suspension was filtered over a glass fiber filter and washed with 20 ml water. The yellow filtrate was evaporated at 40° C./300-10 mbar/2 h to obtain ~1.3 g crude oligo as ammonium salt. The residue were dissolved in 10 ml and treated with 0.28 ml (3.0 mmol, 15 eq) sodium hydroxide 32% in water. The yellow solution were evaporated at 40° C./100-15 mbar/1 h to obtain 0.96 g as yellow solid (contain all cleaved protecting groups) AM-C6-5'-caG*$^{Me}$C*G*t*a*a*a*g*a*g*a*G*G-3' as its Sodium Salt. The yellow solid were suspended in 4.8 ml ethanol, stirred for 1 hour at 40° C., cooled to 20-25° C. and stirred for 1 hour at this temperature. The suspension were filtered and the filter cake were washed with 1.0 ml ethanol and dried at 40° C./15 mbar/1 h to obtain 0.75 g off-white solid (contain all cleaved protecting groups) AM-C6-5'-caG*$^{Me}$C*G*t*a*a*a*g*a*g*a*G*G-3' as its Sodium Salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5197.6.

Example 2F

Preparation of AM-C6-5'-caG*$^{Me}$C*G*t*a*a*a*g*a*g*a*G*G-3' as its Sodium Salt The crude polymer-support bonded Unylinker-LNA-oligo-nucleotide as its diethylamine salt from Example 1F was treated with 25.0 ml conc. aq. ammonium hydroxide solution 30-32%. The suspension was stirred at 60° C. for 10 hour in a pressure stable closed flask. The suspension was filtered over a glass fiber filter and washed with 20 ml water. The yellow filtrates were treated with 0.28 ml (3.0 mmol, 15 eq) sodium hydroxide 32% in water. The yellow solution were evaporated at 40° C./100-15 mbar/1 h to obtain 0.65 g as yellow solid (contain all cleaved protecting groups) AM-C6-5'-caG*$^{Me}$C*G*t*a*a*a*g*a*g*a*G*G-3' as its sodium salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 5197.6.

Example 2G

Preparation of AM-C6-5'-ca$^{Me}$C*$^{Me}$C*t*a*t*t*t*a*a*c*a*t*c*A*G*A*$^{Me}$C-3' as its Sodium Salt The title compound was produced in analogy to Example 2B starting from material ex Example 1G. The obtained orange aqueous solution of 1720 g, which contain in maximum 15.2 mmol product, AM-C6-5'-ca$^{Me}$C*$^{Me}$C*t*a*t*t*t*a*a*c*a*t*c*A*G*A*$^{Me}$C-3' as its sodium salt were used without further purification in the experiment Example 3E. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6357.7.

Example 2H

Preparation of AM-C6-5'-ca$^{Me}$C*T*A*a*t*t*g*t*a*g*t*-a*g*t*a*$^{Me}$C*T*$^{Me}$C-3' as its Sodium Salt The title compound was produced in analogy to Example 2B starting from material ex Example 1H. The obtained orange aqueous solution of 1920 g, which contain in maximum 15.2 mmol product AM-C6-5'-ca$^{Me}$C*T*A*a*t*t*g*t*a*g*t*-a*g*t*a*$^{Me}$C*T*$^{Me}$C-3' as its sodium salt, were used without further purification in the experiment Example 3F. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6748.8

Example 2I

Preparation of AM-C6-5'-ca$^{Me}$C*$^{Me}$C*t*a*t*t*t*a*a*c*a*t*c*A*G*A*$^{Me}$C-3' as its Sodium Salt The title compound was produced via ultrafiltration/diafiltration of 1.00 g of crude CF$_3$CO-AM-C6-5'-c$^{(bz)}$a$^{(bz)Me}$C$^{(bz)}$*T*A$^{(bz)}$*a$^{(bz)}$*t*t*g$^{(ibu)}$*t*a$^{(bz)}$*g$^{(ibu)}$*t*-a$^{(bz)}$*g$^{(ibu)}$*t*a$^{(bz)}$*$^{Me}$C$^{(bz)}$*T*$^{Me}$C$^{(bz)}$-3' as its diethylamine salt from Example 1I was dissolved in water (150 mL) and the resulting solution was diafiltrated on an Äkta-Cross-Flow equiped with two Sartocon Slice Hydrosart 2KD 0.1 m$^2$ membranes using 0.1M NaOH (1.0 L) followed by 0.1M NaHCO$_3$ (1.0 L) and 1M NaCl (1.0 L). A final desalting step was performed with H$_2$O (2.0 L). The resulting solution was concentrated under reduced pressure, triturated with EtOH (5 mL) at room temperature for 1 hour, filtered and dried in vacuo (24° C./10 mbar/12 h) to obtain the title compound as its Sodium Salt (white solid, 410 mg, 40% yield). The material was used without further purification in Example 3G. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6357.7.

Example 2J

Preparation of AM-C6-5'-ca$^{Me}$C*$^{Me}$C*t*a*t*t*t*a*a*c*a*t*c*A*G*A*$^{Me}$C-3' as its Ammonium Salt The title compound was produced starting from material ex Example 1J. The crude polymer-support bonded Unylinker-LNA-oligo-nucleotide as its diethylamine salt from Example 1J was treated with 20 ml conc. aq. ammonium hydroxide solution 30-32%. The suspension was stirred at 45° C. for 10 hour in a pressure stable closed flask.

The suspension was filtered over a glass fiber filter and washed with 10 ml water. The yellow filtrate was evaporated at 40° C./300-10 mbar/2 h to obtain 0.45 g crude oligo as ammonium salt. The identity of the product was determined with UPLC-MS (Waters UPLC ACQUITY H-class, Waters MS SQ Dedector H-class SQD, Column: Waters ACQUITY/ UPLC Oligonucleotides BEH C18 130A 1.7 μm 2.1×50 mm, gradient A: 95% water/2.5% $CH_3OH$/0.2M hexafluoro-2-propanol/16.3 mmol trimethylamine, B: 17.5% water/80% $CH_3OH$/0.2M hexafluoro-2-propanol/16.3 mmol triethylamine). UPLC-MS: m/z 6357.7.

Example 3A

Preparation of GN2-AM-C6*-5'-A*A*T*g*c*t*a*c*a*a*a*a*c*$^{Me}$C*$^{Me}$C*A-3' as its Sodium Salt

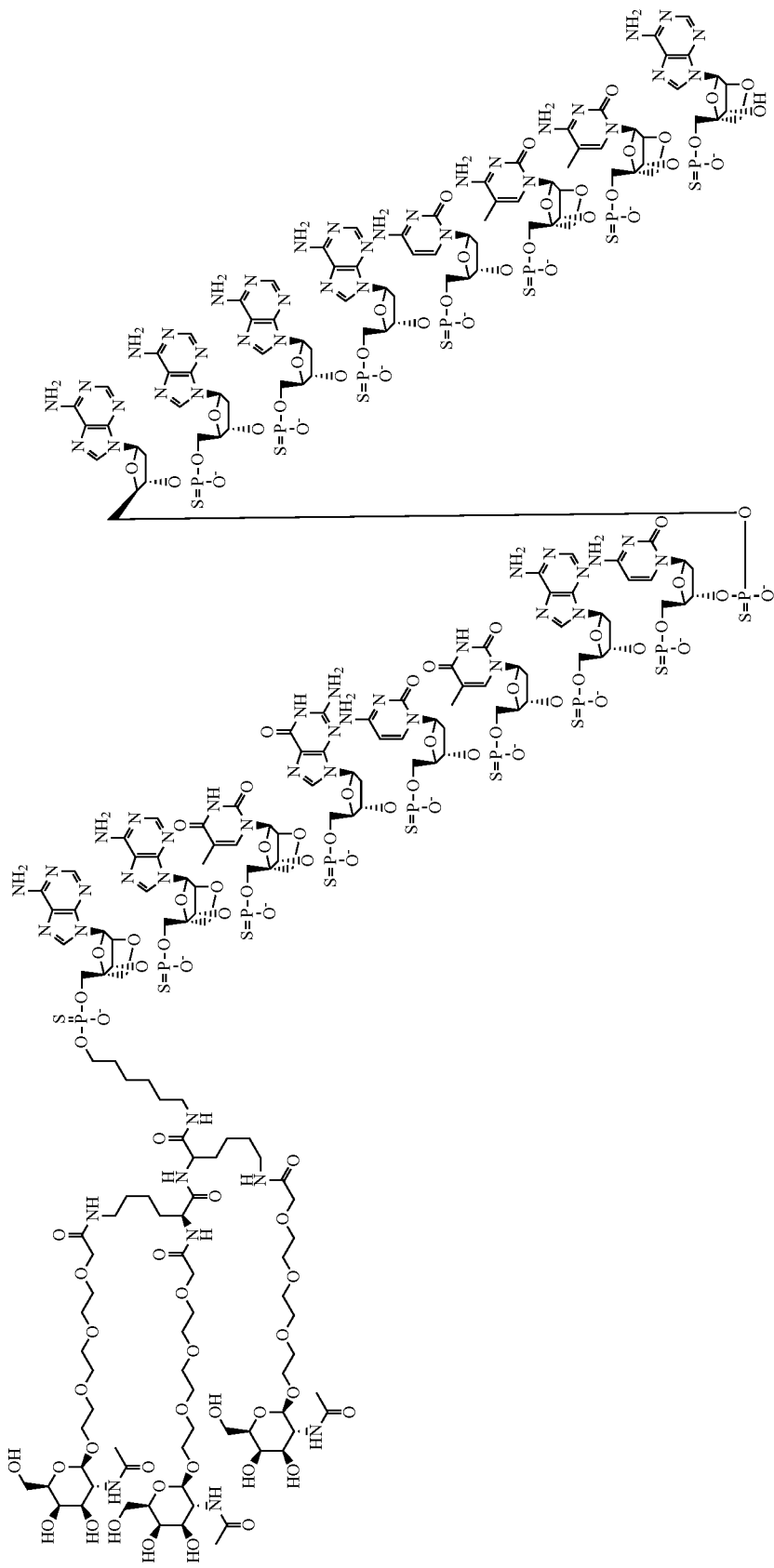

GalNAc Activation:

30.5 g (20.6 mmol) GalNAc-cluster-sodium salt was dissolved in 300 ml DMF, at 20-25° C. a solution of 1.22 ml (18.1 mmol) aq. ortho-phosphoric acid 85% in 300 ml DMF was added in the course of two min. After 5 min. at 20-25° C., 2.61 g (22.7 mmol) N-hydroxysuccinimide was added to the light cloudy colorless solution, followed by addition of 4.75 g (24.8 mmol) EDC·HCl (N-(3-dimethylaminopropyl)-N'-ethylcarbodiimide-hydrochloride). The colorless light cloudy solution were stirred for 3 h at 20-25° C. and used in the coupling step.

GalNAc Coupling:

A preformed solution of 60.0 g (10.3 mmol) AM-C6*-5'-A*A*T*g*c*t*a*c*a*a*a*c*$^{Me}$C*$^{Me}$C*A-3' as its Sodium Salt (from Example 2A) in 900 ml methanol, 30 ml water and 20.7 ml (119 mmol) N-ethyldiisopropylamine was warmed to 40-45° C. and added in 1 min to the former prepared activation solution. The formed yellow suspension was stirred for 0.5 h at 40-45° C. To the yellow suspension 100 ml water was added and the suspension was filtered over a glass fiber filter to yield a clear yellow solution of GN2-AM-C6*-5'-A*A*T*g*c*t*a*c*a*a*a*c*$^{Me}$C*$^{Me}$C*A-3' as its Sodium Salt with a LC-purity of 68.2% area(LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6891.3 which was then purified and isolated in the experiment Example 4A.

Example 3B

Preparation of GN2-AM-C6-5'-caG*$^{Me}$C*G*t*a*a*a*g*a*g*a*G*G-3' as its Sodium Salt

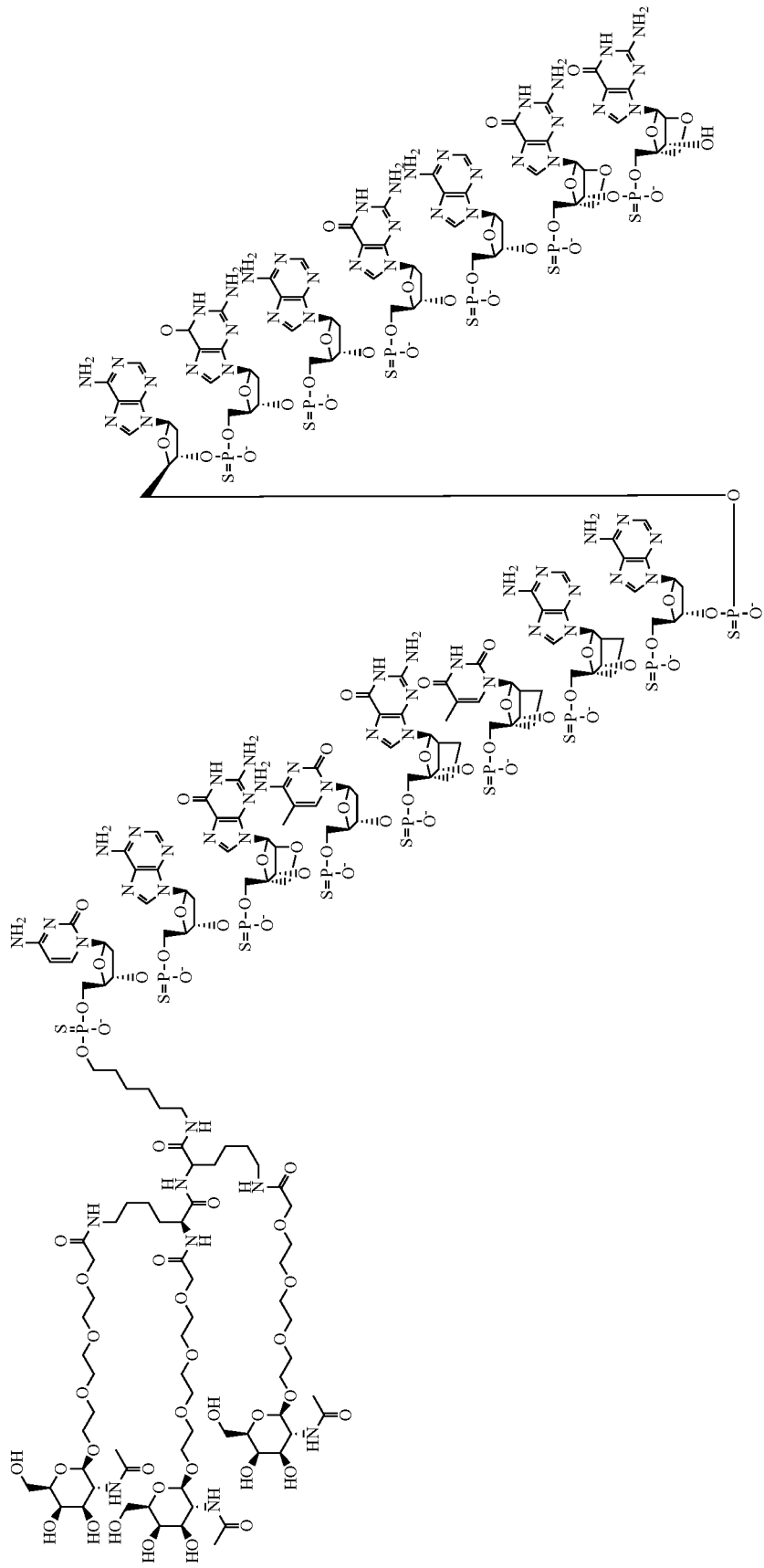

GalNAc Activation:

112.1 g (75.9 mmol) GalNAc-cluster-sodium salt was dissolved in 640 ml DMF, at 20-25° C. a solution of 4.48 ml (66.4 mmol, 1.4 eq) aq. ortho-phosphoric acid 85% in 640 ml DMF was added in the course of two min. After 5 min. at 20-25° C., 13.1 g (114 mmol, 2.4 eq) N-hydroxysuccinimide was added to the light cloudy colorless solution, followed by addition of 21.8 g (24.8 mmol, 2.4 eq) EDC HCl (N-(3-dimethylaminopropyl)-N'-ethylcarbodiimide-hydrochloride). The colorless light cloudy solution were stirred for 4 h at 20-25° C. and used in the coupling step.

GalNac Coupling:

The solution from experiment Example 2B, 855 g (47.5 mmol) AM-C6-5'-caG*$^{Me}$C*G*t*a*a*a*g*a*g*a*G*G-3' as its Sodium Salt was diluted with 3400 ml water, 95.3 ml (546 mmol) N-ethyldiisopropylamine and 2100 ml DMSO were added, the solution was warmed to 40-45° C. and added in 1 min to the former prepared activation solution. The yellow solution was stirred for 0.5 h at 40-45° C. to obtain GN2-AM-C6-5'-caG*C*G*t*a*a*a*g*a*g*a*G*G-3' as its Sodium Salt. HPLC, 46.9% area in crude solution (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6633.3 which was then purified together with 2×20 analogously prepared 1.9 mmol batches (2×38.0 mmol) from the experiment 2B and isolated in the experiment Example 4B1.

Example 3C

Preparation of GN2-AM-C6-5'-caG*$^{Me}$C*G*t*a*a*a*g*a*g*a*G*G-3' as its Sodium Salt The title compound was produced in analogy to Example 3B starting from material ex Example 2C.

The obtained yellow solution of ~275 g, which contain in maximum 1.5 mmol product, GN2-AM-C6-5'-ca$^{Me}$C*$^{Me}$C*t*a*t*t*t*a*a*c*a*t*c*A*G*A*$^{Me}$C-3' as its sodium salt. 230 g of the yellow solution were concentrated with rotary evaporator at 40° C./50 mbar until solution weight of ~115 g. The concentrated yellow solution was cooled to 20-25° C. and added dropwise in the course of 30 min to 230 ml 1-propanol at 20-25° C. The formed white suspension were stirred for 16 hour at 20-25° C. and filtered over a G3 filter. The off-white filter cake were washed with total 50 ml 1-propanol and dried at 40° C./10 mbar for one hour to obtain 9.66 g crude GN2-AM-C6-5'-caG*$^{Me}$C*G*t*a*a*a*g*a*g*a*G*G-3' as its sodium salt, with a HPLC purity 50.3% area. (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6633.3.

Example 3D

Preparation of GN2-AM-C6-5'-caG*$^{Me}$C*G*t*a*a*a*g*a*g*a*G*G-3' as its Sodium Salt The title compound was produced in analogy to Example 3B starting from material ex Example 2D.

GalNAc Activation:

2.54 g (1.72 mmol) GalNAc-cluster-sodium salt was dissolved in 24.0 ml DMF, at 20-25° C. a solution of 0.100 ml (1.50 mmol, 1.175 eq) aq. ortho-phosphoric acid 85% in 24.0 ml DMF was added in the course of two min. After 5 min. at 20-25° C., 0.22 g (1.90 mmol, 2.2 eq) N-hydroxysuccinimide was added to the light cloudy colorless solution, followed by addition of 0.40 g (2.06 mmol, 2.4 eq) EDC·HCl (N-(3-dimethylaminopropyl)-N'-ethylcarbodiimide-hydrochloride). The colorless light cloudy solution were stirred for 3 h at 20-25° C. and used in the coupling step.

GalNAc Coupling:

4.75 g (0.859 mmol) AM-C6-5'-caG*$^{Me}$C*G*t*a*a*a*g*a*g*a*G*G-3' as its Sodium Salt of the solid from experiment Example 2D, was dissolved in 70 ml water, treated with 1.70 ml (9.9 mmol) N-ethyldiisopropylamine and 38 ml DMSO, the solution was warmed to 40-45° C. and added in 1 min to the former prepared activation solution. The yellow solution was stirred for 0.5 h at 40-45° C. to obtain 170 g solution of GN2-AM-C6-5'-caG*$^{Me}$C*G*t*a*a*a*g*a*g*a*G*G-3' as its Sodium Salt. The yellow solution was concentrated with rotary evaporator at 40° C./50 mbar until solution weight of 80 g. The concentrated yellow solution was cooled to 20-25° C. and added dropwise in the course of 30 min to 160 ml 1-propanol at 20-25° C. The formed white suspension were stirred for 2 hour at 20-25° C. and filtered over a G3 filter. The filter cake were washed with total 30 ml 1-propanol and dried at 40° C./20 mbar for one hour to obtain 6.05 g crude GN2-AM-C6-5'-caG*$^{Me}$C*G*t*a*a*a*g*a*g*a*G*G-3' as its Sodium Salt with a HPLC purity 57.2% area. (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6633.3 which was then purified and isolated in the experiments Example 4C and Example 4D.

Example 3E

Preparation of GN2-AM-C6-5'-ca$^{Me}$C*$^{Me}$C*t*a*t*t*t*a*a*c*a*t*c*A*G*A*$^{Me}$C-3' as its Sodium Salt

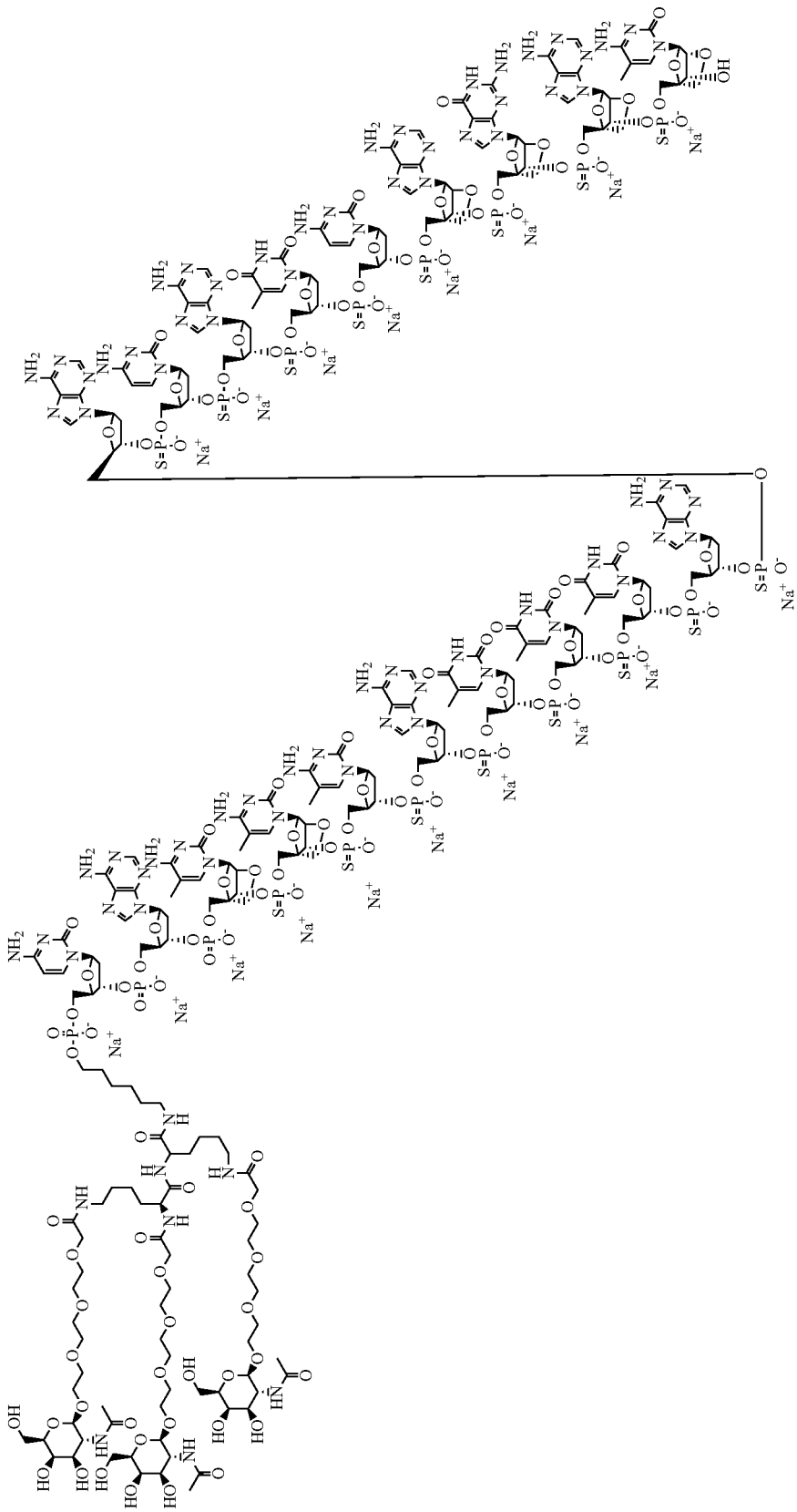

The title compound was produced in analogy to Example 3B starting from material ex Example 2G. The obtained yellow solution of ~3500 g, which contained 15.2 mmol product, GN2-AM-C6-5'-ca$^{Me}$C*$^{Me}$C*t*a*t*t*t*a*a*c*a*t*c*A*G*A*$^{Me}$C-3' as its sodium salt were used without further purification in the experiment Example 4E1.

Example 3F

Preparation of GN2-AM-C6-5'-ca$^{Me}$C*T*A*a*t*t*g*t*a*g*t*-a*g*t*a*$^{Me}$C*T*$^{Me}$C-3' as its Sodium Salt

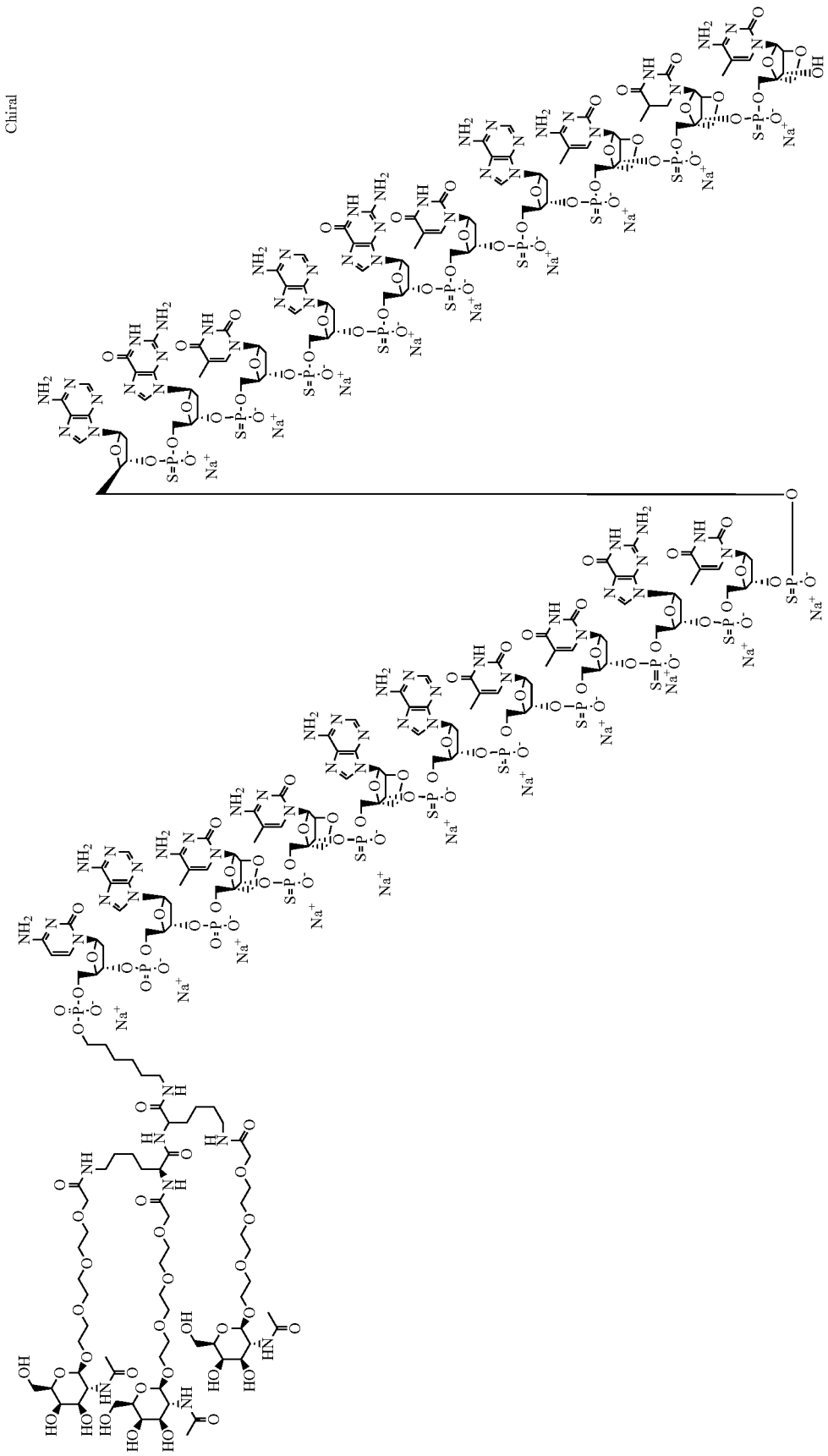

The title compound was produced in analogy to Example 3B starting from material ex Example 2H. The obtained yellow solution of ~3500 g, which contain in maximum 15.2 mmol product, GN2-AM-C6-5'-ca$^{Me}$C*T*A*a*t*t*g*t*a*g*t*a*g*t*a*$^{Me}$C*T*$^{Me}$C-3' as its sodium salt were used without further purification in the experiment Example 4F1

Example 3G

Preparation of GN2-AM-C6-5'-ca$^{Me}$C*$^{Me}$C*t*a*t*t*t*a*a*c*a*t*c*A*G*A*$^{Me}$C-3' as its Sodium Salt The title compound was produced in analogy to Example 3B starting from material ex Example 2I. The yellow solution was concentrated with rotary evaporator at 40° C./50 mbar until solution weight of 4.9 g. The concentrated yellow solution was cooled to 20-25° C. and added dropwise in the course of 5 min to 10 ml 1-propanol at 20-25° C. The formed white suspension were stirred for 12 hour at 20-25° C. and filtered over a G3 filter. The filter cake were washed with total 5 ml 1-propanol and dried at 40° C./20 mbar for one hour to obtain 530 mg crude GN2-AM-C6-5'-ca$^{Me}$C*$^{Me}$C*t*a*t*t*t*a*a*c*a*t*c*A*G*A*$^{Me}$C-3' as its sodium salt with a HPLC purity 57.2% area. (LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7793.4

Example 4A

Purification and Isolation of GN2-AM-C6*-5'-A*A*T*g*c*t*a*c*a*a*a*c*$^{Me}$C*$^{Me}$C*A-3' as its Sodium Salt The solution from Example 3A was purified by ion exchange chromatography (IEX) on a 9 L column packed with Tosoh TSK Gel Super Q-5PW, 30 µm in 2 chromatographic runs. 1.5 L of the crude solution were applied in each run and eluted with a linear gradient from 50 mM NaHCO$_3$ pH 9.0 EtOH 80/20 (mobile phase A) to 50 mM NaHCO$_3$ pH 9.0/EtOH 80/20+1.2M NaCl (mobile phase B).
Gradient:

| Time | Vol-% | |
| --- | --- | --- |
| Minutes | A | B |
| 0 | 100 | 0 |
| 10 | 100 | 0 |
| 11 | 50 | 50 |
| 41 | 10 | 90 |
| 61 | 10 | 90 |
| 62 | 100 | 0 |
| 77 | 100 | 0 |

Flow rate: 0.8 L/min
Detection: 290 nm
Temperature: 20-25° C.

Fractions were collected according to the elution profile. Fractions were pooled (9 L) and concentrated by ultrafiltration (UF).

The UF was conducted on 2×0.57 (1.14 m$^2$ Pellicon2 3kD membrane from Millipore. The solution of 9 L was concentrated to ca. 3 L and diafiltered on a Amicon SP 20 UF unit with 20 L water to a final conductivity of the permeate of 35 µS/cm.

The solution was lyophilized in one lyophilization cycle on a Lyostar II lyophilizer in a lyoguard tray resulting in 43 g dry white powder. After conditioning at 21-22° C. and 38-42% rel. humidity for 4 days, a total of 46.4 g of GN2-AM-C6*-5'-A*A*T*g*c*t*a*c*a*a*a*c*$^{Me}$C*$^{Me}$C*A-3' was isolated as its Sodium Salt as a white amorphous powder with a water content of 12.7% and 90.2% purity LC-System Agilent Technologies 1290 Infinity, Column: Waters ACQUITY/UPLC Oligonucleotides BEH C18 130A 1.7 µm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine).

With the aid of 2D-$^1$H/$^{13}$C-NMR spectroscopy of the linker domain, an epimer ratio GN2a to GN2b (see page 17) of ~64% to ~36% was detected. The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6891.3.

Example 4B1

Purification of GN2-AM-C6-5'-caG*$^{Me}$C*G*t*a*a*a*g*a*g*a*G*G-3' as its Sodium Salt The solution from Example 3B was purified by IEX chromatography on a 9 L column packed with Tosoh TSK Gel Super Q-5PW, 30 µm in 47 chromatographic runs. 0.4 L of the crude solution were applied in each run and eluted with a linear gradient from 50 mM NaHCO$_3$ pH 9.0 EtOH 80/20 (mobile phase A) to 50 mM NaHCO$_3$ pH 9.0/EtOH 80/20+1.2M NaCl (mobile phase B).
Gradient:

| Time | Vol-% | |
| --- | --- | --- |
| Minutes | A | B |
| 0 | 100 | 0 |
| 10 | 100 | 0 |
| 11 | 50 | 50 |
| 41 | 10 | 90 |
| 42 | 0 | 100 |
| 52 | 0 | 100 |
| 53 | 100 | 0 |
| 70 | 100 | 0 |

Flow rate: 0.8 L/min
Detection: 290 nm
Temperature: 20-25° C.

Fractions were collected according to the elution profile. Fractions were pooled (220 L) and concentrated by ultrafiltration (UF).

The UF was conducted on 2×0.57 (1.14 m² Pellicon2 3kD membrane from Millipore. The solution of 220 L was concentrated to ca. 3 L and diafiltered on a Amicon SP 20 UF unit with 20 L water to a final conductivity of the permeate of <50 μS/cm.

The resulting concentrate can be either lyophilized directly (3-step process) or further purified by reversed phase chromatography (RP) as described in Example 4B2

The solution from above was lyophilized in one lyophilization cycle on a Lyostar II lyophilizer in two lyoguard trays resulting in 174 g dry white powder.

After conditioning at 21° C. and 50% rel. humidity for 2 days, a total of 203.9 g of GN2-AM-C6*-5'-A*A*T*g*c*t*a*c*a*a*a*c*$^{Me}$C*$^{Me}$C*A-3' was isolated as its Sodium Salt as a white amorphous powder with a water content of 16.2% and a purity of 89.0% area (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). With aid of 2D-$^1$H/$^{13}$C-NMR spectroscopy of the linker domain, an epimer ratio GN2a to GN2b (see page 17) of ~43.9% to ~56.1% was detected. The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 6633.3.

Example 4B2

1.6 g of the lyophilized powder from Example 4B1 was further purified using reversed phase chromatography (RP).

The material was dissolved in 16 ml 0.2M sodium acetate and separated in two chromatographic runs on a YMC Triart prep C8-S, 10 μm 250×30 mm column. 8 ml of the solution were applied in each run and eluted with a linear gradient from 0.2M sodium acetate (mobile phase A) to acetonitrile (mobile phase B).
Gradient:

| Time | Vol-% | |
| --- | --- | --- |
| Minutes | A | B |
| 0 | 95 | 5 |
| 2 | 95 | 5 |
| 22 | 80 | 20 |
| 23 | 20 | 80 |
| 28 | 20 | 80 |
| 29 | 95 | 5 |
| 34 | 95 | 5 |

Flow rate: 30 mL/min
Detection: 290 nm
Temperature: 20-25° C.

Fractions were collected according to the elution profile. Fractions were pooled, concentrated and diafiltered by ultrafiltration (UF) on an Amicon Ultra-15 centrifugal filter, 3kD. The resulting concentrate was lyophilized resulting in 0.9 g white amorphous powder with a purity of 93.9% a/a determined with the analytical method described in Example 4B1.

Example 4C

The order of the chromatographic purifications is interchangeable. A purification starting with reversed phase chromatography (RP) followed by ion exchange chromatography (IEX) results in the same yields and purities as conduction first the IEX and afterwards the RP chromatography.

1$^{st}$ chromatography-RP: 1 g from experiment Example 3D was dissolved in 10 ml 0.2M sodium acetate and purified using reversed phase (RP) chromatography in 50 chromatographic runs on a YMC Triart prep C18-S, 10 μm 250×4.6 mm column. 0.2 ml of the solution were applied in each run and eluted with a linear gradient from 0.2M sodium acetate (mobile phase A) to acetonitrile (mobile phase B).
Gradient:

| Time | Vol-% | |
| --- | --- | --- |
| Minutes | A | B |
| 0 | 95 | 5 |
| 2 | 95 | 5 |
| 27 | 85 | 15 |
| 27.1 | 20 | 80 |
| 32 | 20 | 80 |
| 32.1 | 95 | 5 |
| 37 | 95 | 5 |

Flow rate: 0.7 mL/min
Detection: 310 nm
Temperature: 45° C.

Fractions were collected according to the elution profile. Fractions were pooled (250 ml), concentrated (150 ml) and diafiltered with 1.5 L water by ultrafiltration (UF) on a GE cross flow unit equipped with a 0.1 m² Millipore Pellicon II membrane (3 kDa). The resulting concentrate was lyophilized resulting in 0.375 g white amorphous powder with a purity of 91.3% a/a determined with the analytical method described in Example 4B1.

2$^{nd}$ chromatography—IEX: 0.355 g of this material were further purified by anion exchange chromatography. The material was dissolved in 10 ml 50 mM sodium bicarbonate pH9.0/EtOH 80/20 and purified in 11 runs on a column packed with Tosoh TSK Gel Super Q-5PW, 30 μm (10×220 mm) with a linear gradient from 50 mM NaHCO$_3$ pH 9.0 EtOH 80/20 (mobile phase A) to 50 mM NaHCO$_3$ pH 9.0/EtOH 80/20+1.2M NaCl (mobile phase B). Gradient:

| Time | Vol-% | |
| --- | --- | --- |
| Minutes | A | B |
| 0 | 100 | 0 |
| 10 | 100 | 0 |
| 11 | 50 | 50 |
| 41 | 10 | 90 |
| 44 | 10 | 90 |
| 44.1 | 0 | 100 |
| 58 | 0 | 100 |
| 58.1 | 100 | 0 |
| 68 | 100 | 0 |

Flow rate: 1.3 mL/min
Detection: 300 nm
Temperature: 30° C.

Fractions were collected according to the elution profile. Fractions were pooled (150 ml) and diafiltered with 1.5 L water by ultrafiltration (UF) on a GE cross flow unit equipped with a 0.1 m² Millipore Pellicon II membrane (3 kDa). The resulting concentrate was lyophilized resulting in 0.246 g white amorphous powder with a purity of 92.8% a/a determined with the analytical method described in Example 4B1.

Example 4D

1st chromatography—IEX: 1 g of from experiment Example 3D was dissolved in 10 ml 0.2M sodium acetate and purified in 34 runs on a column packed with Tosoh TSK Gel Super Q-5PW, 30 μm (10×220 mm) with a linear gradient from 50 mM NaHCO₃ pH 9.0 EtOH 80/20 (mobile phase A) to 50 mM NaHCO₃ pH 9.0/EtOH 80/20+1.2M NaCl (mobile phase B).
Gradient:

| Time | Vol-% | |
|---|---|---|
| Minutes | A | B |
| 0 | 100 | 0 |
| 10 | 100 | 0 |
| 11 | 50 | 50 |
| 41 | 10 | 90 |
| 44 | 10 | 90 |
| 44.1 | 0 | 100 |
| 58 | 0 | 100 |
| 58.1 | 100 | 0 |
| 68 | 100 | 0 |

Flow rate: 1.3 mL/min
Detection: 300 nm
Temperature: 30° C.

Fractions were collected according to the elution profile. Fractions were pooled (250 ml), concentrated (150 ml) and diafiltered with 1.5 L water by ultrafiltration (UF) on a GE cross flow unit equipped with a 0.1 m² Millipore Pellicon II membrane (3 kDa). The resulting concentrate was lyophilized resulting in 0.292 g white amorphous powder with a purity of 87.7% a/a determined with the analytical method described in Example 4B1.

2$^{nd}$ chromatography—RP: 0.272 g of this material were dissolved in 3 ml 0.2M sodium acetate and purified using reversed phase (RP) chromatography in 18 chromatographic runs on a YMC Triart prep C18-S, 10 μm 250×4.6 mm column. 0.18 ml of the solution were applied in each run and eluted with a linear gradient from 0.2M sodium acetate (mobile phase A) to acetonitrile (mobile phase B).
Gradient:

| Time | Vol-% | |
|---|---|---|
| Minutes | A | B |
| 0 | 95 | 5 |
| 2 | 95 | 5 |
| 27 | 85 | 15 |
| 27.1 | 20 | 80 |
| 32 | 20 | 80 |
| 32.1 | 95 | 5 |
| 37 | 95 | 5 |

Flow rate: 0.7 mL/min
Detection: 310 nm
Temperature: 45° C.

Fractions were collected according to the elution profile. Fractions were pooled (150 ml) and diafiltered with 1.5 L water by ultrafiltration (UF) on an GE cross flow unit equipped with a 0.1 m² Millipore Pellicon II membrane (3 kDa). The resulting concentrate was lyophilized resulting in 0.19 g white amorphous powder with a purity of 93.7% a/a determined with the analytical method described in Example 4B1.

Example 4E1

The solution from Example 3E was purified by IEX chromatography on a 9 L column packed with Tosoh TSK Gel Super Q-5PW, 30 μm in 8 chromatographic runs. 0.3-0.38 L of the crude solution were applied in each run and eluted with a linear gradient from 50 mM NaHCO₃ pH 9.0 EtOH 80/20 (mobile phase A) to 50 mM NaHCO₃ pH 9.0/EtOH 80/20+1.2M NaCl (mobile phase B).
Gradient:

| Time | Vol-% | |
|---|---|---|
| Minutes | A | B |
| 0 | 100 | 0 |
| 10 | 100 | 0 |
| 11 | 45 | 55 |
| 41 | 10 | 90 |
| 42 | 0 | 100 |
| 52 | 0 | 100 |
| 53 | 100 | 0 |
| 70 | 100 | 0 |

Flow rate: 0.8 L/min
Detection: 294 nm
Temperature: 20-25° C.

Fractions were collected according to the elution profile. Fractions were pooled (48 L) and concentrated by ultrafiltration (UF).

The UF was conducted on 2×0.1 m² Sartocon Slice Hydrosart membrane from Sartorius. The solution of 48 L was concentrated to 1.4 L and diafiltered on a GE cross flow UF unit with water to a final conductivity of the permeate of <50 μS/cm.

The solution was lyophilized in one lyophilization cycle on a Lyostar II lyophilizer in one lyoguard tray resulting in 51 g dry white powder. After conditioning at 21° C. and 50% rel. humidity for 2 days, a total of 60.5 g of GN2-AM-C6-5'-ca$^{Me}$C*$^{Me}$C*t*a*t*t*t*a*a*c*a*t*c*A*G*A*$^{Me}$C-3' was isolated as its Sodium Salt as a white amorphous powder with a water content of 15.7% and a purity of 85.4% area (LC-System Agilent Technologies 1290 Infinity, Column: Waters ACQUITY/UPLC Oligonucleotides BEH C18 130A 1.7 μm 2.1×50 mm, 260 nm, gradient A: Water/CH₃OH/0.2M hexafluoro-2-propanol/triethylamine, B: Water/CH₃OH/0.2M hexafluoro-2-propanol/triethylamine). With aid of 2D-$^1$H/$^{13}$C-NMR spectroscopy of the linker domain, an epimer ratio GN2a to GN2b (see page 17) of ~50.8% to ~49.2% was detected. The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH₃OH/0.2M hexafluoro-2-propanol/16.3 mmol trimethylamine, B: 17.5% water/80% CH₃OH/0.2M hexafluoro-2-propanol/16.3 mmol triethylamine). UPLC-MS: m/z 7793.4.

Example 4E2

0.5 g of the lyophilized powder from example 4E1 were further purified using RP chromatography.

The material was dissolved in 3.3.ml 0.2M sodium acetate and separated in 33 chromatographic runs on a YMC Triart prep C8-S, 10 μm 250×4.6 mm column. 0.1 ml of the solution were applied in each run and eluted with a linear gradient from 0.2M sodium acetate (mobile phase A) to acetonitrile (mobile phase B).

Gradient:

| Time | Vol-% | |
|---|---|---|
| Minutes | A | B |
| 0 | 94 | 6 |
| 2 | 94 | 6 |
| 22 | 84 | 16 |
| 22.1 | 20 | 80 |
| 25 | 20 | 80 |
| 25.1 | 94 | 6 |
| 35 | 94 | 6 |

Flow rate: 0.7 mL/min
Detection: 290 nm
Temperature: 45° C.

Fractions were collected according to the elution profile. Fractions were pooled (100 ml), diluted with water (400 ml), concentrated (150 ml) and diafiltered with 1.5 L water by ultrafiltration (UF) on an GE cross flow unit equipped with 2×0.1 m² Sartocon Slice Hydrosart membrane from Sartorius. The resulting concentrate was lyophilized resulting in 0.29 g white amorphous powder with a purity of 91.9% a/a determined with the analytical method described in Example 4E1.

Example 4E3

5.0 g of GN2-AM-C6-5'-ca$^{Me}$C*$^{Me}$C*t*a*t*t*t*a*a*c*a*t*c*A*G*A*$^{Me}$C-3' with a purity of 85.4% a/a were prepared and purified in analogy to Example 4E1. The material was then further purified by RP chromatography, UF and isolated via lyophilization in analogy to Example 4E2 to yield 2.5 g of GN2-AM-C6-5'-ca$^{Me}$C*$^{Me}$C*t*a*t*t*t*a*a*c*a*t*c*A*G*A*$^{Me}$C-3' with a purity of 89.8% a/a. After the material was dissolved in 50 ml water the colorless solution was then spray dried on a Procept spray drier (120° C.) to yield 1.8 g of GN2-AM-C6-5'-ca$^{Me}$C*$^{Me}$C*t*a*t*t*t*a*a*c*a*t*c*A*G*A*$^{Me}$C-3' with a purity of 89.5% a/a determined with the analytical method described in Example 4E1. No analytical hinds by LC/MS, NMR and EA (elemental analysis) techniques were found that during spray drying the material underwent (partial) decomposition. As a consequence thereof, material isolation after IEX and/or RP chromatography and subsequent UF can be conducted either via spray drying or lyophilisation.

Example 4E4

A solution (7.2 ml) of crude GN2-AM-C6-5'-ca$^{Me}$C*$^{Me}$C*t*a*t*t*t*a*a*c*a*t*c*A*G*A*$^{Me}$C-3' with a purity of 55.4% a/a—which was prepared in analogy to Example 3E—was diluted with 14.4 ml 0.2M sodium acetate and purified in 36 chromatographic runs on a YMC Triart C8 prep 120, 10 μm 250×4.6 mm column. Thereby 0.6 ml fractions of the solution were applied per run and eluted with a linear gradient from 0.2M sodium acetate (mobile phase A) to acetonitrile (mobile phase B).

Gradient:

| Time | Vol-% | |
|---|---|---|
| Minutes | A | B |
| 0 | 95 | 5 |
| 2 | 95 | 5 |
| 22 | 85 | 15 |
| 22.1 | 20 | 80 |
| 27 | 20 | 80 |
| 27.1 | 95 | 5 |
| 34 | 95 | 5 |

Flow rate: 0.7 mL/min
Detection: 300 nm
Temperature: 45° C.

Target fractions were pooled (50 ml) and concentrated by ultrafiltration on a 0.1 m2 Sartocon Slice Hydrosart membrane from Sartorius on a GE cross flow UF unit and diafiltered with water to a final conductivity of the permeate of <50 μS/cm. The solution was lyophilized to yield 120 mg of GN2-AM-C6-5'-ca$^{Me}$C*$^{e}$C*t*a*t*t*t*a*a*c*a*t*c*A*G*A*$^{Me}$C-3' with a purity of 87.6% a/a determined with the analytical method described in Example 4E1.

Example 4F1

The solution from Example 3F was purified via IEX chromatography on a 9 L column packed with Tosoh TSK Gel Super Q-5PW, 30 μm in 8 chromatographic runs. 0.35 L of the crude solution were applied in each run and eluted with a linear gradient from 50 mM NaHCO$_3$ pH 9.0 EtOH 80/20 (mobile phase A) to 50 mM NaHCO$_3$ pH 9.0/EtOH 80/20+1.2M NaCl (mobile phase B).

Gradient:

| Time | Vol-% | |
|---|---|---|
| Minutes | A | B |
| 0 | 100 | 0 |
| 10 | 100 | 0 |
| 11 | 40 | 60 |
| 41 | 10 | 90 |
| 42 | 0 | 100 |
| 52 | 0 | 100 |
| 53 | 100 | 0 |
| 70 | 100 | 0 |

Flow rate: 0.8 L/min
Detection: 294 nm
Temperature: 20-25° C.

Fractions were collected according to the elution profile. Fractions were pooled (29 L) and concentrated by ultrafiltration (UF).

The UF was conducted on 2×0.1 m² Sartocon Slice Hydrosart membrane from Sartorius. The solution of 29 L was concentrated to 3.2 L and diafiltered with water on a GE cross flow UF unit to a final conductivity of the permeate of <50 μS/cm.

The solution was lyophilized in one lyophilization cycle on a Lyostar II lyophilizer in two lyoguard trays resulting in 43 g dry white powder.

After conditioning at 21° C. and 50% rel. humidity for 2 days, a total of 50.2 g of GN2-AM-C6-5'-ca$^{Me}$C*T*A*a*t*t*g*t*a*g*t*-a*g*t*a*$^{Me}$C*T*$^{Me}$C-3' was isolated as its Sodium Salt as a white amorphous powder with a water content of 16.4% and a purity of 85.0% area (LC-System Agilent Technologies 1290 Infinity, Column: Waters ACQUITY/UPLC Oligonucleotides BEH C18 130A 1.7 μm 2.1×50 mm, 260 nm, gradient A: Water/CH$_3$OH/0.2M hexafluoro-2-propanol/triethylamine, B: Water/CH$_3$OH/0.2M hexafluoro-2-propanol/triethylamine). With aid of 2D-$^1$H/$^{13}$C-NMR spectroscopy of the linker domain, an epimer ratio GN2a to GN2b (see page 17) of ~49.3% to ~50.7% GN2b was detected. The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 μm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 8184.4.

Example 4F2

0.5 g of the lyophilized powder from Example 4F1 was further purified using RP chromatography.

The material was dissolved in 3.3.ml 0.2M sodium acetate and separated in 33 chromatographic runs on a YMC Triart prep C8-S, 10 μm 250×4.6 mm column. 0.1 ml of the solution were applied in each run and eluted with a linear gradient from 0.2M sodium acetate (mobile phase A) to acetonitrile (mobile phase B).

Gradient:

| Time | Vol-% | |
| --- | --- | --- |
| Minutes | A | B |
| 0 | 94 | 6 |
| 2 | 94 | 6 |
| 22 | 84 | 16 |
| 22.1 | 20 | 80 |
| 25 | 20 | 80 |
| 25.1 | 94 | 6 |
| 35 | 94 | 6 |

Flow rate: 0.7 mL/min
Detection: 290 nm
Temperature: 45° C.

Fractions were collected according to the elution profile. Fractions were pooled (100 ml), diluted with water (400 ml), concentrated (150 ml) and diafiltered (1.5 L water) by ultrafiltration (UF) on a GE cross flow unit equipped with 2×0.1 m$^2$ Sartocon Slice Hydrosart membrane from Sartorius. The resulting concentrate was lyophilized resulting in 0.29 g white amorphous powder with a purity of 91.9% a/a determined with the analytical method described in Example 4F1.

Example 5

Synthesis of GN2-AM-C6-5'-ca$^{Me}$C*$^{Me}$C*t*a*t*t*t*a*a*c*a*t*c*A*G*A*$^{Me}$C-3' as its Sodium Salt Step 1: Preparation of CF$_3$CO-AM-C6-5' c$^{(bz)}$a$^{(bz)Me}$C$^{(bz)}$*$^{Me}$C$^{(bz)}$*G$^{(dmf)}$*t*a$^{(bz)}$*t*t*a$^{(bz)}$*a$^{(bz)}$*c$^{(bz)}$*a$^{(bz)}$*t*c$^{(bz)}$*A$^{(bz)}$*G$^{(dmf)}$*A$^{(bz)}$-3' UnyLinker as its Diethylammonium Salt Nomenclature: A, G, T,$^{Me}$C (5-methyl cytosine)=LNA; a,t,c,g=DNA; *=phosphorthioate as diastereomer mix; AM-C6=Aminolinker C6; GN2=GalNAc-cluster; CF$_3$CO=TFA=trifluoroacetyl; bz=benzoyl; ibu=isobutyryl; dmf=dimethylformamidine The title compound was produced by standard phosphoramidite chemistry on solid phase at a scale of 1.90 mmol using an AEKTA Oligopilot 100 (GE Healthcare, Freiburg, Germany) and Primer Support Unylinker (Kinovate Nittophase®HL UnyLinker™400, USA). Oligonucleotides containing LNA, i.e. 2'-OCH$_2$-4' bridged nucleotide monomers (Sigma-Aldrich, SAFC, Hamburg, Germany) and DNA nucleoside monomers (Sigma-Aldrich, SAFC, Hamburg, Germany) were generated employing the corresponding phosphoramidites and TFA-protected-aminolinker-phosphoramidites (Link Technologies, Scotland, UK). In general 1.5 eq of the DNA/LNA-phosphoramidites and 2.0 eq TFA-aminolinker-phosphoramidite per coupling were employed. Phosphorothiolation reagent (Xanthanhydride), 3-amino-1,2,4-dithiazole-5-thione (ABCR, AB251827) was used as a 0.1M solution in anhydrous acetonitrile/pyridine 1/1. All other standard reagent solution (DCA-debloc, BTT, Cap A,B1,B2, Oxidizer, DEA wash, were commercially available (Sigma-Aldrich, Merck Millipore, EMP Biotech; see details below). Deprotection of 2-cyanoethyl-group was achieved by washing with diethylamine in anhydrous acetonitrile (DEA-wash), to obtain crude protected polymer-support bonded Unylinker-LNA-oligo-nucleotide as diethylammonium salt. The thereby obtained title compound was used without further operation in the Experiment 2.

Standard Reagent Solutions

| | |
| --- | --- |
| DCA-deblock | 3% Dichloroacetic acid in toluene (v/v) |
| BTT activator | 0.3M 5-Benzylthiotetrazol in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Oxidizer | 0.05M Water/pyridine/iodine 10/90/1.27 (v/v/w) |
| Thiolation | 0.1M 3-amino-1,2,4-dithiazole-5-thione in pyridine/MeCN 1:1 (v/v) |
| DEA wash | 20% Diethylamine in acetonitrile (v/v) |

Step 2: Preparation of AM-C6-5'-ca$^{Me}$C*$^{Me}$C*t*a*t*t*t*a*a*c*a*t*c*A*G*A*$^{Me}$C-3' as its Sodium Salt The crude polymer-support bonded Unylinker-LNA-oligo-nucleotide as its diethylammonium salt from Experiment 1 was treated with 180 ml conc. aq. ammonium hydroxide solution 30-32%. The suspension was stirred at 60° C. for 10 hour in a pressure stable closed flask. The suspension was filtered over a glass fiber filter and washed with 60 ml water. The yellow filtrate was evaporated at 40° C./300-10 mbar/2 h to obtain ~14.5 g crude oligo as ammonium salt. The identity of the product was determined with UPLC-MS (Waters UPLC ACQUITY H-class, Waters MS SQ Dedector H-class SQD, Column: Waters ACQUITY/UPLC Oligonucleotides BEH C18 130A 1.7 μm 2.1×50 mm, gradient A: 95% water/2.5% $CH_3OH$/0.2M hexafluoro-2-propanol/16.3 mmol trimethylamine, B: 17.5% water/80% $CH_3OH$/0.2M hexafluoro-2-propanol/16.3 mmol triethylamine). UPLC-MS: m/z 6362.1. A total of 51 analogously prepared 1.9 mmol batches and two 3.8 mmol batches were combined with the above's one (total new batch size: 106.7 mmol) and dissolved in 4.0 L water in one round bottom flask. The orange solution was treated with 189 ml 10.8M NaOH (2.04 mol, 19.1 eq). The precipitated solids were filtered off, washed with 200 ml water and the filtrate was concentrated at 40° C./200-60 mbar to obtain ~1.5 kg crude solution which was treated with 2 L water and the same volume was distilled off in vacuo 40° C./50 mbar, this procedure were repeated twice until the distillate reached a pH of 7-7.5 which indicated the absence of ammonia. The suspension was diluted with water to give 10 kg of a suspension which was filtered again, the solids washed with 200 ml of water to afford 9.67 kg of a brown solution (containing a theoretical 7.4% of crude product (w/w)) which was used in several batches without further purification.

Step 3: Preparation of 1, RO7191863-001, GN2-AM-C6-
5'ca$^{Me}$C*$^{Me}$C*t*a*t*t*t*a*a*c*a*t*c*A*G*A*$^{Me}$C-3' as its Sodium Salt GalNAc Activation:

82.6 g (55.9 mmol) GalNAc-cluster-sodium salt was dissolved in 600 ml DMF at 20-25° C. and a solution of 3.3 ml (48.9 mmol, 1.13 eq) aq. phosphoric acid 85% in 600 ml DMF was added in the course of two min. After 5 min. at 20-25° C., 9.66 g (83.9 mmol, 1.94 eq) N-hydroxysuccinimide was added to the colorless solution, followed by addition of 16.1 g (84 mmol, 1.94 eq) EDC HCl (N-(3-dimethylaminopropyl)-N'-ethylcarbodiimide-hydrochloride)[1]. The colorless slightly cloudy solution was stirred for 4 h at 20-25° C. and used in the coupling step.

GalNAc Coupling:

To 3.95 kg of the solution from experiment Example 2 theoretically containing 292 g (43.3 mmol) AM-C6-5'-ca$^{Me}$C*$^{Me}$C*t*a*t*t*t*a*a*c*a*t*c*A*G*A*$^{Me}$C-3' as its Sodium Salt was added 70.3 ml (402 mmol) N-ethyldiisopropylamine and 1.98 L DMSO, the solution was warmed to 40-45° C. and added in 1 min to the activated GalNAc solution from above. The yellow solution was stirred for 0.5 h at 40-45° C. to obtain a crude solution of GN2-AM-C6-5'-ca$^{Me}$C*$^{Me}$C*t*a*t*t*t*a*a*c*a*t*c*A*G*A*$^{Me}$C-3' as its Sodium Salt. HPLC showed 56.5% area in crude solution (LC-System Agilent Technologies 1290 Infinity, Column: Waters ACQUITY/UPLC Oligonucleotides BEH C18 130A 1.7 μm 2.1×50 mm, 260 nm, gradient A: Water/$CH_3OH$/0.2M hexafluoro-2-propanol/triethylamine, B: Water/$CH_3OH$/0.2M hexafluoro-2-propanol/triethylamine).

This solution was stored at 4° C. until purification. Upon storage, precipitation of residual benzamide occurred which was filtered off prior to purification. This procedure was repeated once on the same scale and once on half scale and the three individual reaction mixtures were combined for purification.

Step 4: Purification & Isolation of GN2-AM-C6-5'-ca$^{Me}$C*$^{Me}$C*t*a*t*t*t*a*a*c*a*t*c*A*G*A*$^{Me}$C-3' as its Sodium Salt The solution obtained from the GalNAc coupling reaction was purified using reversed phase chromatography. A 15 cm ID DAC column was packed with 2.5 kg YMC Triart prep C8-S to 80 bar column pressure. The feed solution was prepared by diluting the crude coupling reaction with 0.2M sodium acetate solution 50/50 v/v and completely separated in 77 runs by gradient elution (Injection: 400 ml feed solution. Gradient: A: 0.2M sodium acetate, B: acetonitrile) Gradient:

| Time | Vol-% | |
| --- | --- | --- |
| Minutes | A | B |
| 0 | 95 | 5 |
| 2 | 95 | 5 |
| 22 | 85 | 15 |
| 22.1 | 20 | 80 |
| 27 | 80 | 90 |
| 27.1 | 95 | 5 |
| 34 | 95 | 5 |

The gradient was stopped after elution of the target peak. Flow rate: 700 mL/min Detection: 300 nm
Temperature: 45° C.

The chromatogram indicates the gradient as well as the fraction cuts. The main target fraction was collected between c4 and c5, while side fractions were collected between other cuts.

All fractions were collected in pools.

Pool 1 collected between c2 and c3 was discarded, while the other pools were concentrated and desalted by ultrafiltration on 2×Pellicon 3 Kassetten 0.57 m2.

Concentration: Inlet pressure: 3.0 bar; Outlet pressure: 0.5 bar; Permeat flow: 200 ml/min Desalting: Inlet pressure: 3.0 bar; Outlet pressure: 0.5 bar; Permeat flow: 50 ml/min The main target pool of 70 L was concentrated to 3 L, diafiltrated to a conductivity of <100uS/cm and lyophilized in two lyoguards resulting in 188 g of lyophilized powder (88.70 % a/a). However, at the final concentration the material started to pass the membrane.

The side fraction pools were combined and concentrated and diafiltrated as before and lyophilized separately resulting in 120 g lyophilized powder (88.62% a/a).

In order to obtain homogeneous material both batches were combined, dissolved in 3 L of water and again lyophilized resulting in 305 g lyophilized powder (88.80% a/a).

As the material is very hygroscopic the lyoguards are conditioned after lyophilization in a climate chamber at 21° C. and 50% rel humidity until weight was constant, which was achieved after 48 h.

After conditioning, a total of 355 g of GN2-AM-C6-5'-ca$^{Me}$C*$^{Me}$C*t*a*t*t*t*a*a*c*a*t*c*A*G*A*$^{Me}$C-3' as its Sodium Salt with 90.35% purity and a water content of 16% was isolated in an overall yield of 30.7% The purity of the product was determined with HPLC (LC-System Agilent Technologies 1290 Infinity Series LC129; Column: Waters ACQUITY/UPLC Oligonucleotides BEH C18 130A 1.7 µm 2.1×50 mm,; Column temp: 80° C.; Sampler temp: 15° C.; Flow rate 0.4 mL/min; Detection 210 nm/260 nm; Mobile phase A: 200 mM hexafluoro-2-propanol+5 mM hexylamine+4 mM triethylamine+40 µL H$_3$PO$_4$; Mobile phase B: 90% MeOH/10% acetonitrile.
Gradient:

| Time | Vol-% | |
|---|---|---|
| Minutes | A | B |
| 0 | 100 | 0 |
| 1 | 100 | 0 |
| 4 | 85 | 15 |
| 26 | 74 | 26 |
| 40 | 5 | 95 |
| 45 | 5 | 95 |
| 46 | 100 | 0 |
| 53 | 100 | 0 |

The identity of the product was determined with UPLC-MS (Waters UPLC ACQUITY H-class, Waters MS SQ Detector H-class SQD, Column: Waters ACQUITY/UPLC Oligonucleotides BEH C18 130A 1.7 µm 2.1×50 mm, gradient A: 95% water/2.5% CH$_3$OH/0.2M hexafluoro-2-propanol/16.3 mmol trimethylamine, B: 17.5% water/80% CH$_3$OH/0.2M hexafluoro-2-propanol/16.3 mmol triethylamine). UPLC-MS: m/z 7793.4.

The invention claimed is:

1. A process for the preparation of a GalNAc cluster oligonucleotide conjugate, the process comprising the steps of:
   a) producing an oligonucleotide or an aliphatic amine salt thereof bound to a solid phase support;
   b) cleaving the oligonucleotide from the support and removing the protecting groups in the presence of ammonia, thereby providing the ammonium salt of the unprotected oligonucleotide;
   c) removing free ammonia or residual aliphatic amine from step b) by
      (i) performing a salt exchange change from the ammonium salt of the oligonucleotide to form an aqueous solution comprising an alkali metal salt, an earth alkali metal salt, or a tetraalkylammonium salt of the oligonucleotide, wherein said salt exchange is performed by contacting the oligonucleotide with an alkali metal hydroxide, an earth alkali metal hydroxide, or a tetraalkylammonium hydroxide or halide, and
      (ii) isolating the alkali metal salt, earth alkali metal salt, tetraalkylammonium salt of the oligonucleotide from the aqueous solution by;
         1) evaporating the water and subsequent aceotropic removal of remaining water with the help of a suitable organic solvent;
         2) continuous partial evaporation (by constant volume and addition of water) until the pH of the vapor phase reaches pH 7;
         3) tangential flow filtration against aqueous alkali metal salt or earth alkali metal salt solutions; or
         4) anion-exchange chromatography followed by desalting and concentration via tangential flow filtration;
   d) coupling the alkali metal salt, the earth alkali metal salt, or the tetraalkylammonium salt of the oligonucleotide with a GalNAc cluster compound or salt thereof, thereby preparing the GalNAc cluster oligonucleotide conjugate; and
   e) purifying the GalNAc-cluster oligonucleotide conjugate from step d), the purification comprising the sequence of steps:
   1) anion exchange chromatography or reversed phase chromatography;
   2) tangential flow filtration; and
   3). lyophilization or spray drying; or
   1) anion exchange chromatography or reversed phase chromatography;
   2) tangential flow filtration;
   3) anion exchange chromatography or reversed phase chromatography;
   4) tangential flow filtration; and
   5) lyophilization or spray drying.

2. Process of claim 1, wherein the oligonucleotide is a 5' amino-modified oligonucleotide.

3. Process of claim 2, wherein the 5'amino-modifier is selected from an optionally amino group protected amino $C_{2-12}$- alkyl linker or amino ethylene glycol linker containing 1 to 10 ethylene glycol units.

4. Process of claim 1, wherein the oligonucleotide consists of optionally modified DNA, RNA or LNA nucleoside monomers or combinations thereof and is 7 to 30 nucleotides in length.

5. Process of claim 1 wherein the oligonucleotide consists of DNA or LNA nucleoside monomers or combinations thereof and is 10 to 25 nucleotides in length.

6. Process of claim 1 wherein in step a) the aliphatic amine salt is a mono-, di- or tri-$C_{1-4}$-alkylamine or cyclic aliphatic amine salt.

7. Process of claim 6, wherein the diethyl amine salt is formed.

8. Process of claim 1 wherein in step b) aqueous ammonia is used.

9. Process of claim 1 wherein the coupling in step d) is performed with a GalNAc cluster compound of formula

I

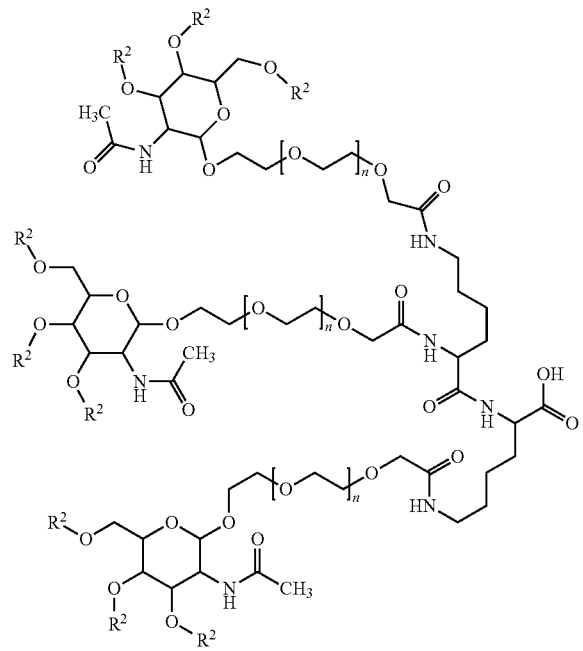

wherein $R^2$ is hydrogen or a hydroxy protecting group and n is an integer from 0 to 10, corresponding salts, enantiomers and/ stereoisomers thereof.

10. Process of claim 9, wherein the GalNAc cluster compound of formula I is an alkali metal or earth alkali metal salt of the formula Ia.

Ia

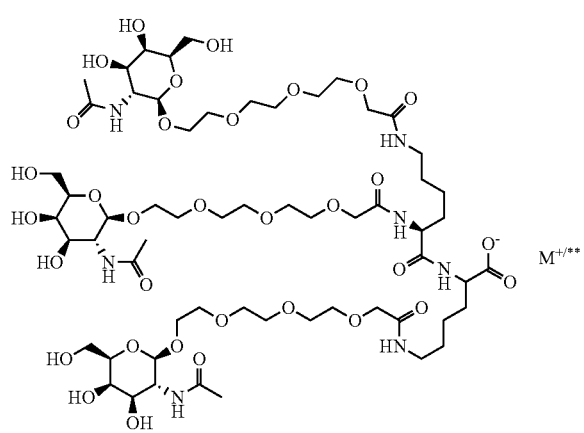

wherein $M^{+/++}$ is the cation of an alkali metal or of an earth alkali metal.

11. Process of claim 1 wherein the coupling of the oligonucleotide with the GalNAc cluster compound or with a salt thereof in step d) encompasses in a first step the activation of the GalNAc cluster compound with a coupling agent and in a second step the coupling of the activated GalNAc cluster compound with the oligonucleotide in the presence of an amine base and an organic solvent.

12. Process of claim 11, wherein the coupling agent is a coupling agent selected from DCC (N,N'-dicyclohexylcarbodiimide) or EDC (N-(3-dimethylaminopropyl)-N'-ethylcarbodiimide-hydrochloride) or TBTU (N,N,N',N'-tetramethyl-O-(benzotriazol-1-yl)uronium tetrafluoroborate, HBTU (2-(1H-benzotriazol-1-yl)-1,1,3,3-tetramethyluronium hexafluorophosphate) and an additive selected from HOBt (1-hydroxybenztriazole), HOSu (N-hydroxysuccinimide) or HOAt (1-hydroxy-7-azabenzotriazole and combinations thereof.

13. Process of claim 11 wherein the amine base is a tertiary amine, the organic solvent is a polar aprotic solvent, and the coupling is performed at a reaction temperature in the range of 20° C. and 70° C.

14. Process of claim 11, wherein the coupling agent is n-propylphosphonic acid anhydride (T3P) or (3-(diethoxyphosphoryloxy)-1,2,3-benzo[d]triazine-4(3H)-one (DEPBT) together with a tertiary amine.

15. Process of claim 1 wherein the purification of the GalNAc-cluster oligonucleotide conjugate in step e) comprises, the steps chromatography, concentration and isolation.

16. Process of claim 1, wherein the oligonucleotide is:
AM-C6*-5'-A*A*T*g*c*t*a*c*a*a*a*a*c*$^{Me}$C*$^{Me}$C*A-3' (Compound 1);
AM-C6-5'-caG*$^{Me}$C*G*t*a*a*a*g*a*g*a*G*G-3' (Compound 2);
AM-C6-5'-ca$^{Me}$C*$^{Me}$C*t*a*t*t*t*a*a*c*a*-t*c*A*G*A*$^{Me}$C-3' (Compound 5); or
AM-C6-5'-ca$^{Me}$C*T*A*a*t*t*g*t*a*g*t*-a*g*t*a*$^{Me}$C*T*$^{Me}$C-3' (Compound 6), wherein
AM-C6 is a C6 amino linker;
* stands for phosphorthioate bridges;
A, G, T and $^{Me}$C (5-methyl cytosine) are LNA nucleoside monomers; and
a, t, c, g are DNA nucleoside monomers.

17. Process of claim 1, wherein the GalNAc cluster oligonucleotide conjugate is:
GN2-AM-C6*-5'-A*A*T*g*c*t*a*c*a*a*a*a*c*$^{Me}$C*$^{Me}$C*A-3' (Compound 3);
GN2-AM-C6-5'-caG*$^{Me}$C*G*t*a*a*a*g*a*g*a*G*G-3' (Compound 4);
GN2-AM-C6-5'-ca$^{Me}$C*$^{Me}$C*t*a*t*t*t*a*a*c*a*-t*c*A*G*A*$^{Me}$C-3' (Compound 7); or
GN2-AM-C6-5'-ca$^{Me}$C*T*A*a*t*t*g*t*a*g*t*-a*g*t*a*$^{Me}$C*T*$^{Me}$C-3' (Compound 8), wherein
AM-C6 is a C6 amino linker;
* stands for phosphorthioate bridges;
A, G, T and $^{Me}$C (5-methyl cytosine) are LNA nucleoside monomers;
a, t, c, g are DNA nucleoside monomers; and
GN2 is the GalNAc cluster.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide Sequence

<400> SEQUENCE: 1
aatgctacaa aaccccca                                                    18

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide Sequence

<400> SEQUENCE: 2
cagcgtaaag agagg                                                       15

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide Sequence

<400> SEQUENCE: 3
cacctattta acatcagac                                                   19

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Sequence

<400> SEQUENCE: 4
cactaattgt agtagtactc                                                  20